(12) United States Patent
Demierre et al.

(10) Patent No.: US 9,040,463 B2
(45) Date of Patent: May 26, 2015

(54) ASSAY DEVICE AND METHOD FOR PERFORMING BIOLOGICAL ASSAYS

(75) Inventors: Nicolas Demierre, Corseaux (CH); Nader Donzel, Ecublens (CH); Jose Gil, Ecublens (CH); Philippe Renaud, Lausanne (CH)

(73) Assignee: MYCARTIS NV, Zwijnaarde/Ghent (BG)

( * ) Notice: Subject to any disclaimer, the term of this patent is extended or adjusted under 35 U.S.C. 154(b) by 401 days.

(21) Appl. No.: 13/141,570

(22) PCT Filed: Dec. 23, 2009

(86) PCT No.: PCT/CH2009/000412
§ 371 (c)(1),
(2), (4) Date: Jun. 22, 2011

(87) PCT Pub. No.: WO2010/072011
PCT Pub. Date: Jul. 1, 2010

(65) Prior Publication Data
US 2011/0306506 A1 Dec. 15, 2011

Related U.S. Application Data

(60) Provisional application No. 61/140,328, filed on Dec. 23, 2008.

(51) Int. Cl.
*G01N 33/543* (2006.01)
*B01L 3/00* (2006.01)

(52) U.S. Cl.
CPC ..... *G01N 33/54373* (2013.01); *B01J 2219/005* (2013.01); *B01J 2219/00556* (2013.01); *B01L 3/502761* (2013.01); *B01L 2200/0647* (2013.01); *B01L 2300/0654* (2013.01); *B01L 2400/0424* (2013.01); *B01L 2400/043* (2013.01); *B01L 2400/0487* (2013.01)

(58) Field of Classification Search
USPC ...................................................... 506/7, 39
See application file for complete search history.

(56) References Cited

U.S. PATENT DOCUMENTS

| | | | |
|---|---|---|---|
| 2006/0119913 A1* | 6/2006 | Moon | 359/2 |
| 2006/0252867 A1 | 11/2006 | Tang et al. | |
| 2008/0176216 A1 | 7/2008 | Doyle et al. | |
| 2008/0234144 A1 | 9/2008 | Ho | |
| 2009/0035793 A1 | 2/2009 | Nishino et al. | |

FOREIGN PATENT DOCUMENTS

| | | |
|---|---|---|
| EP | 1 276 555 | 11/2004 |
| EP | 1 712 282 | 10/2006 |
| WO | 99/24458 | 5/1999 |
| WO | 00/01475 | 1/2000 |
| WO | 00/61198 | 10/2000 |
| WO | 02/059603 A2 | 8/2002 |
| WO | 2004/025560 | 3/2004 |
| WO | 2007/076132 A2 | 7/2007 |
| WO | 2008/063758 A2 | 5/2008 |

OTHER PUBLICATIONS

Pamme and Manz, Analytical Chem, 2004, 76, , p. 7250-7256.*
Fan et al, Analytical Chem, 1999, 71, p. 4851-4859.*
NG, "Rapid descrimination of single-nucleotide mismatches using a microfluidic device with monolayered beads", Analytica Chimica Acta, 2007, pp. 295-303.
Search report from International Search Report and Written Opinion for International Application PCT/CH2009/000412, mail date is Apr. 5, 2010.
Abstract of paper entitled Optimisation of a silicon/silicon dioxide substrate for a fluorescence DNA microarray. Biosensors & bioelectronics, 2004. 20(4): p. 797-806 by Bras, M., et al.
Abstract of paper entitled Enhanced sensitivity detection of protein immobilization by fluorescent interference on oxidized silicon. Biosensors and Bioelectronics, 2003. 19(5): p. 457-464) by Volle, J. N., et al.

* cited by examiner

*Primary Examiner* — Jennfier McDonald
*Assistant Examiner* — Valerie Toodle
(74) *Attorney, Agent, or Firm* — Kusner & Jaffe

(57) ABSTRACT

The invention provides a multiplexed assay device comprising a reaction chamber and several sets of encoded microcarriers 2 wherein the reaction chamber is a microchannel 1 and wherein the longitudinal movement of the microcarriers 2 is restricted and wherein the microcarriers 2 have a shape in relation to the geometry of the microchannel 1 such that at least two can stand side by side in the microchannel 1 without touching each other and without touching the perimeter of the microchannel 1 and are preferably observable in the reaction chamber. Moreover, the invention provides a method for performing multiplexed assay based on microcarriers 2 that improves mass transfer, simplifies the preparation and the execution of the assay and facilitates readout of biological reactions and identity of microcarriers 2.

13 Claims, 17 Drawing Sheets

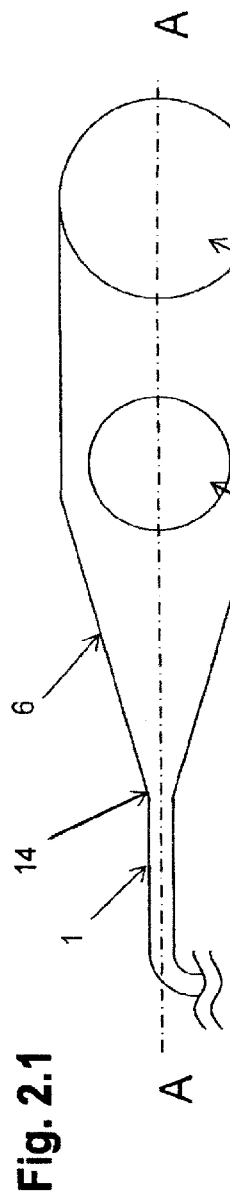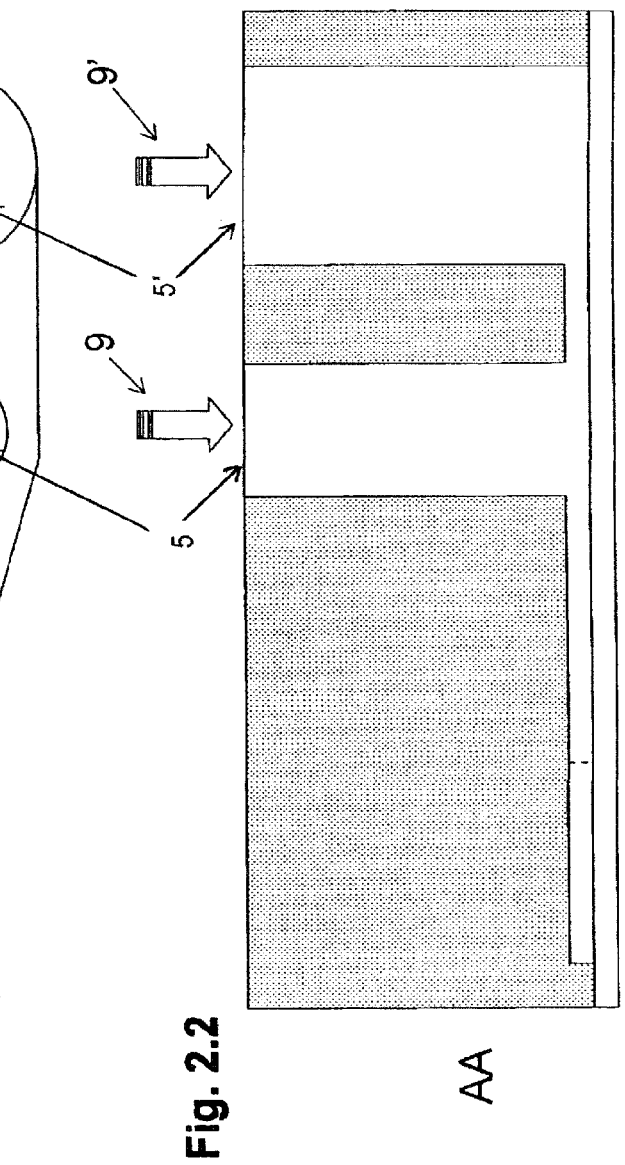
Fig. 2.1
Fig. 2.2
Fig. 2

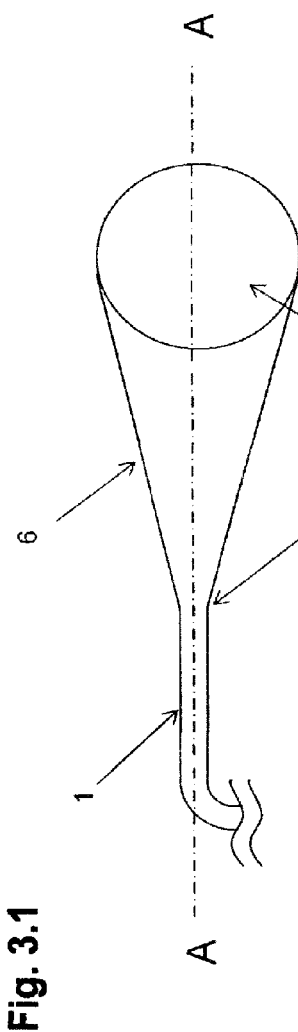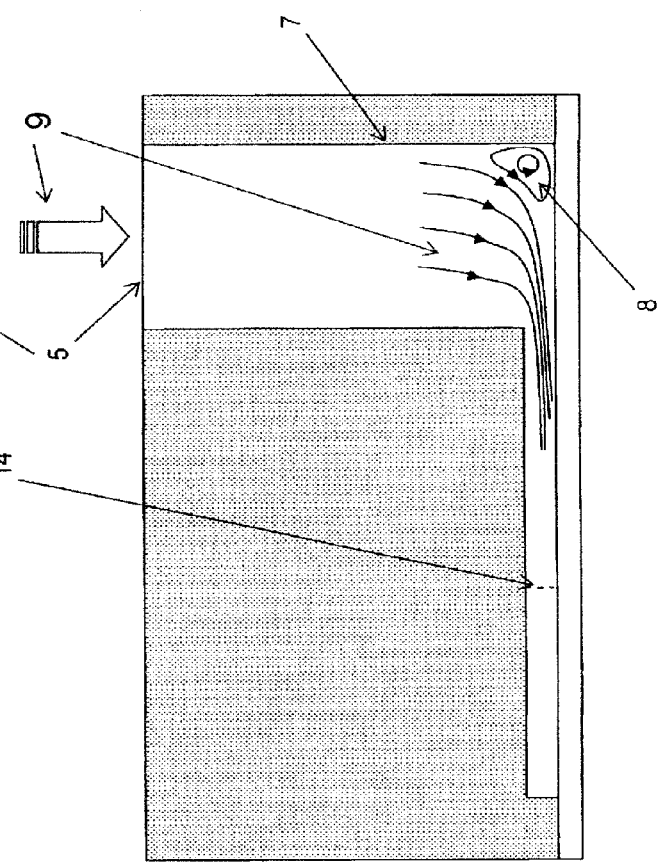
Fig. 3.1
Fig. 3.2
Fig. 3

SEQUENCE LISTING

```
<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1 caacccagc taatattatt                                                  20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2
tgggtaagtt agggcgatgg                                                 20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
aataatatta gctggggttg                                                 20
```

ASSAY DEVICE AND METHOD FOR PERFORMING BIOLOGICAL ASSAYS

RELATED APPLICATIONS

This application is a U.S. National Stage Application of International Application No. PCT/CH09/00412, filed Dec. 23, 2009, which claims the benefit of U.S. Provisional Application No. 61/140,328, filed Dec. 23, 2008.

SEQUENCE LISTING

The instant application contains a Sequence Listing which has been submitted in ASCII format via EFS-Web and is hereby incorporated by reference in its entirety. Said ASCII copy, created on Aug. 3, 2011, is named P40221.txt and is 1,070 bytes in size.

TECHNICAL FIELD

The invention relates to assay technology in the life science industry and in particular to multiplexing applied in diagnostics, genomic research and molecular biology. The invention uses techniques and processes of microfabrication technology as well as from semi-conductor technology.

BACKGROUND ART

Biological assays allow the detection of target molecules in a biological sample. Typically, the detection of target molecules is performed by using solid surfaces (e.g. microarrays or bottom of wells) or nanocarrier or microcarrier structures that are functionalized with detection molecules (ligands) designed to bind to specific targets.

One challenge of the biological assay technologies is the acceleration of mass transfer taking place during an assay. The problem of mass transfer is further exacerbated in multiplexed assays, where multiple target molecules are sought simultaneously in a single biological sample since the relative density of each probe is lower than in a single assay.

In order to overcome the limitations of mass transfer, different setups were described such as performing the multiplexed assays in a microchannel, thereby reducing the diffusion distance between the targets and the probes. For example, J. K.-K. Ng et al (2007), Anal. Chem Acta 582, pp. 295-303, describe a microfluidic device comprising microbeads being functionalized with oligonucleotides via biotin-streptavidin binding. The microfluidic device consists of a broad chamber with a varying section and with a weir to trap the microbeads in a monolayered arrangement. Different sets of microbeads are sequentially introduced separated by unfunctionalized spacer beads. As can be seen from FIG. 5a in the document, the microbeads form large groups with undefined boundaries due to particle mixing with particles of the spacer sets. Since the beads have no characteristic which distinguishes them from each other, such as size, shape or a code, the boundaries of the different sets are unknown and only become revealed after the assay by the detection of the presence of the analyte in the sample. Therefore, the setup described by J. K.-K. Ng et al is not suited for multiplexed assays, as it is not possible to reliably determine the presence or absence of several targets in a sample. For example, in the absence of several analytes in the sample which correspond to consecutive sets, no signal will be recorded in an entire portion of the microchannel. It will thus be difficult to establish how many sets this portion actually corresponds to (thus there will be no indication on how many analytes are actually absent). It will also be difficult or even impossible to establish the identity of the subsequent analytes that react with the consecutive sets since the position in the sequence of these sets cannot be established reliably.

EP1712282A2, WO00/061198A1 and WO04/025560A1 describe setups having microcarrier elements placed inside microchannels such as their movement is restricted in the microchannel. Assays are performed by flowing fluids through. This type of setup is effective for mass transfer since diffusion distances are small and the movement of the sample relative to the microcarriers brings the target molecules to the proximity of the receptor molecules. This type of setups also reduces cost by reducing the amount of reagents that are needed.

However, in EP1712282A2 and WO00/061198A1, the order of the microcarriers in the microchannel is very important since it defines the identity of the microcarriers. In WO2004025560A1, the microcarriers are encoded so that their order in the microchannel is not as critical as in EP1712282A2. Still, the disclosure of WO2004025560A1 only describes configurations where the microcarriers are strictly aligned behind each other in order to meet the requirements of the proposed decoding mechanism that requires a specific placement of the microcarriers' codes for allowing their identification.

EP1712282A2, WO00/061198A1 and WO04/025560A1 describe setups that are not easy to prepare in practice because they require a very controlled introduction of microcarriers in a confined space, either to control their order or to align them for the decoding purpose. To achieve such configurations, specialized methods and specific settings involving microscopy, micromanipulation (use of microscopically controlled forces) and/or microfabrication techniques are required.

Indeed, the microcarriers need to be introduced in the microchannel by some process that involves either intricate micromanipulation of individual microcarriers such as described in WO0061198A1 or, when the exact position of each microcarrier does not need to be controlled, some kind of funnel mechanism that guides them from a bulk into a small microchannel such as described in WO04/025560A1. The funnel mechanism is simpler to build in practice but is sensitive to clogging by forming arches in the entry of the microchannel 1 (FIGS. 13 and 14). Further to the funnel approach, WO04/025560A1 suggests the production of assay sticks by a sandwich approach wherein the beads are placed on a lower plate having grooves. Subsequently, an upper plate is laid on top and attached to the lower plate.

One practical consequence of the level of sophistication required to prepare the setups described in the prior art is that it reduces the possibility of being used to produce flexible configuration for research use by a laboratory technician. For example, it would be very difficult to allow the preparation of custom-made configurations by a laboratory technician that would like to use its own biochemical coating procedures on microcarriers (for example to test biological probes that are in development) and then introduce them in the setup to perform biological assays.

Therefore, there is a need in the art for assay devices and methods which improve the mass transfer in biological multiplexing assays based on microcarriers and simplify the overall procedure for preparing the setup, executing the biological assay and performing the necessary readouts.

DISCLOSURE OF THE INVENTION

Hence, it is a general object of the invention to provide a device and a method which allow for improved mass transfer and simplification of the procedure for preparation and performance of biological multiplexed assays, in particular a device and method for multiplexed assays.

The present invention provides a microchannel as a reaction chamber comprising simultaneously several sets of encoded microcarriers (i.e. microparticles having ligands attached to their surface) such as the shape and size of the microcarriers relative to the cross-section of the microchannel allows to have, over the entire length of the microchannel, at least two of any of the microcarriers arranged side by side without touching each other and without touching the perimeter of the microchannel when travelling in the longitudinal direction of the microchannel, e.g. during filling. Preferably, the microcarriers can be observed within the microchannel. The set-up also comprises some means to restrict the longitudinal movement of said microcarriers in said microchannel while still letting the fluids flow through. The biological sample, typically comprising one or more target molecules, is flown through the confined or immobilized microcarriers, so that the microcarriers do not follow the flow of the biological sample. The movement of the sample relative to the microcarriers brings the target molecules to the proximity of the receptor molecules, increasing the chances of binding and hence reducing the incubation time needed to perform the mass transfer. In order to distinguish the various sets independently of the performance of an assay and independently of their position, the microcarriers are encoded such as the code is indicative of their function.

An important aspect of the invention lies on the relative shape and size of the microcarriers in relation to the cross-section of the microchannel, in order to facilitate the preparation of the setup. The existing art described in EP1712282A2, WO00/061198A1 and WO04/025560A1 requires a strict control of the arrangement of the microcarriers in the microfluidic channel which is not easy to achieve as the manipulation of objects of such small size (i.e. in the micron range) is not trivial and requires specialized methods and specific settings involving microscopy, micromanipulation (use of microscopically controlled forces) and/or microfabrication techniques.

In the present invention, the microcarriers have a much higher freedom of movement inside the microchannel. The shape size of microcarriers of the invention is such that at least two microcarriers can be placed side by side without touching each other and without touching the perimeter of the microchannel, over the entire length of the microchannel serving as a reaction chamber and notably at its entry. This means that microcarriers that would be moving in the longitudinal direction of the microchannel at different speeds would be able to pass each other until the point where their longitudinal movement is restricted. This feature is key to facilitate the practical construction of the setup, which is particularly important when the setup is prepared in a research environment just before performing an assay, which allows flexibility in preparing mixes of sets of microcarriers. The use of a microchannel that is relatively much wider than the size of the microcarriers has the effects of decreasing the likelihood of forming arches at the entry of the microchannel that would clog the entry. This further allows for using an enlarged inlet instead of a narrow funnel to load the microchannel. A second advantage consists in reducing the chances of blocking a large portion of the microcarriers if there are obstacles inside the microchannel. Obstacles could be undesired elements such as debris (dust) or air bubbles in the microchannel or could be built-in features that might be necessary to facilitate the microfabrication of the microfluidic channel, e.g. pillars for ensuring the proper rigidity of microchannels when using soft polymers such as PDMS.

The invention further provides a method for performing an assay based on microcarriers and suitable for multiplexing comprising the steps of
 a) providing an assay device comprising a microchannel as reaction chamber and providing at least two sets of encoded microcarriers, wherein the code of the microcarriers is indicative of the function and wherein the shape and size of said microcarriers relative to the cross-section of the microchannel allows to have, over the entire length of the microchannel, at least two of any of the microcarriers standing side by side without touching each other and without touching the perimeter of the microchannel;
 b) at least partially filling said microchannel with said at least two sets of encoded microcarriers;
 c) restricting the movement of said microcarriers in the longitudinal direction of said microchannel while still letting the fluids flow through;
 d) flowing a sample potentially comprising one or more target molecules through said microchannel comprising said microcarriers;
 e) identifying the sets of microcarriers; and
 f) detecting a reaction between the ligand and the target molecule and correlating the presence or absence of a reaction with the identity of a specific set to infer the presence or absence of a target molecule in the sample.

In traditional solutions, such as using multiple wells, mass transfer is improved using basic agitation techniques, whereby both the sample and the microcarrier elements are agitated randomly. At micro scales, where the flows are laminar, this technique only marginally increases the relative movement of the microcarriers with regard to the sample, which is a key element to ensure an efficient mass transfer. The present invention decouples the movements of the sample and the microcarriers. Moreover, the elongated reaction chamber setup and the limited volume around the microcarriers ensure that the sample passes close by a maximum number of microcarriers. The achieved advantage of the assay and method disclosed herein is to speed the mass transfer by reducing the reliance on diffusion to contact molecules of interest with potential receptors. Other advantages include the simplicity of the mechanism, which relies on the properties of microchannels and geometrical arrangements to improve mass transfer. The setup also allows for flexible fluidic manipulations with minimum requirements for the handling of the microcarriers, for example if further steps are required for the performance of complex assays. Little adaptation of the setup is needed if it is desired to move the fluid back and forth, for example if the speed of the fluid cannot be controlled reliably or if the sample is diluted it may so that it needs to be passed several times in contact with the microcarriers to ensure proper capture of molecules of interest.

The invention is suitable for multiplexed assays as it allows the association of various functions to various sets of microcarriers and using them simultaneously in an assay while still being able to discriminate the various reactions provided that the reaction generates a signal that is co-localized in the microcarrier. This is done by working with encoded microcarriers that are identifiable and therefore allow determining which function they carry.

Furthermore, the microfluidic setup reduces the amount of sample needed to carry out the biological assay. It also facilitates the execution of any needed additional assay steps by allowing additional reagents or washing solutions to be flown through the microchannel without having to perform any particular manipulation on the microcarriers.

The invention also simplifies the overall manipulations required to obtain the results of the essay compared to traditional microcarriers-based approaches where the microcarriers need to be collected from the reaction chamber and moved to a reading device. Indeed, in those embodiments where the microchannel is at least partially transparent, the microcarriers can be observed directly inside the microchannel by optical means to identify the sets and perform the biological readout. This configuration also enables the possibility of kinetic information by observing the microcarriers as the reaction occurs.

Furthermore, the invention also simplifies the preparation of the assay device by facilitating the manipulation and reducing the level of expertise required for introducing the microcarriers in the microchannel, thus enabling the use of custom made configurations that are prepared just before performing the assay (for example in research environments).

The invention can predominantly be used in the life science industry, and in particular in diagnostics, genomic research and molecular biology.

BRIEF DESCRIPTION OF THE DRAWINGS

The invention will be better understood and objects other than those set forth above will become apparent when consideration is given to the following detailed description thereof. Such description makes reference to the annexed drawings, wherein:

FIG. 1.1 depicts a top-view, whereas FIG. 1.2 shows a cross-sectional view through the line A-A of FIG. 1.1

FIG. 2 depicts an exemplary embodiment of a microchannel having an entry 14 with an enlarged extremity 6 and two inlets 5 and 5'. FIG. 2.1 depicts a top-view of the microchannel 1 with the enlarged section 6 and two inlets 5 and 5', whereas FIG. 2.2 shows a cross-sectional view through the line A-A of FIG. 2.1.

FIG. 3 depicts an exemplary embodiment of a microchannel 1 having an entry 14 with an enlarged extremity 6 and one inlet 5. The figure also shows laminar flows and a laminar vortex 8 in the well 7. FIG. 3.1 shows a top view of the microchannel 1 and its enlarged section 6 at one extremity of the microchannel 1. FIG. 3.2 represents a cross-sectional view through the line A-A of FIG. 3.1 and shows the inlet 5 and the well 7 that gives access to the microchannel 1 as well as the flow 9 forming a vortex 8.

FIG. 4.1 shows a top view whereas FIG. 4.2 shows a cross-section view through the line A-A of FIG. 4.1. FIG. 4.3 shows a 3-D representation. In the illustrated case, the monolayer arrangement is not strictly in a plane (the vertical position of the microcarriers 2 can slightly vary as shown in FIG. 4.2) but the microcarriers 2 cannot go on top of each other. Different filling patterns of the microcarriers 2 illustrate different sets.

FIG. 6.1 shows a top view whereas FIG. 6.2 shows a cross-section view through the line A-A of FIG. 6.1. FIG. 6.3 shows a 3-D representation.

MODES FOR CARRYING OUT THE INVENTION

Figure 1:
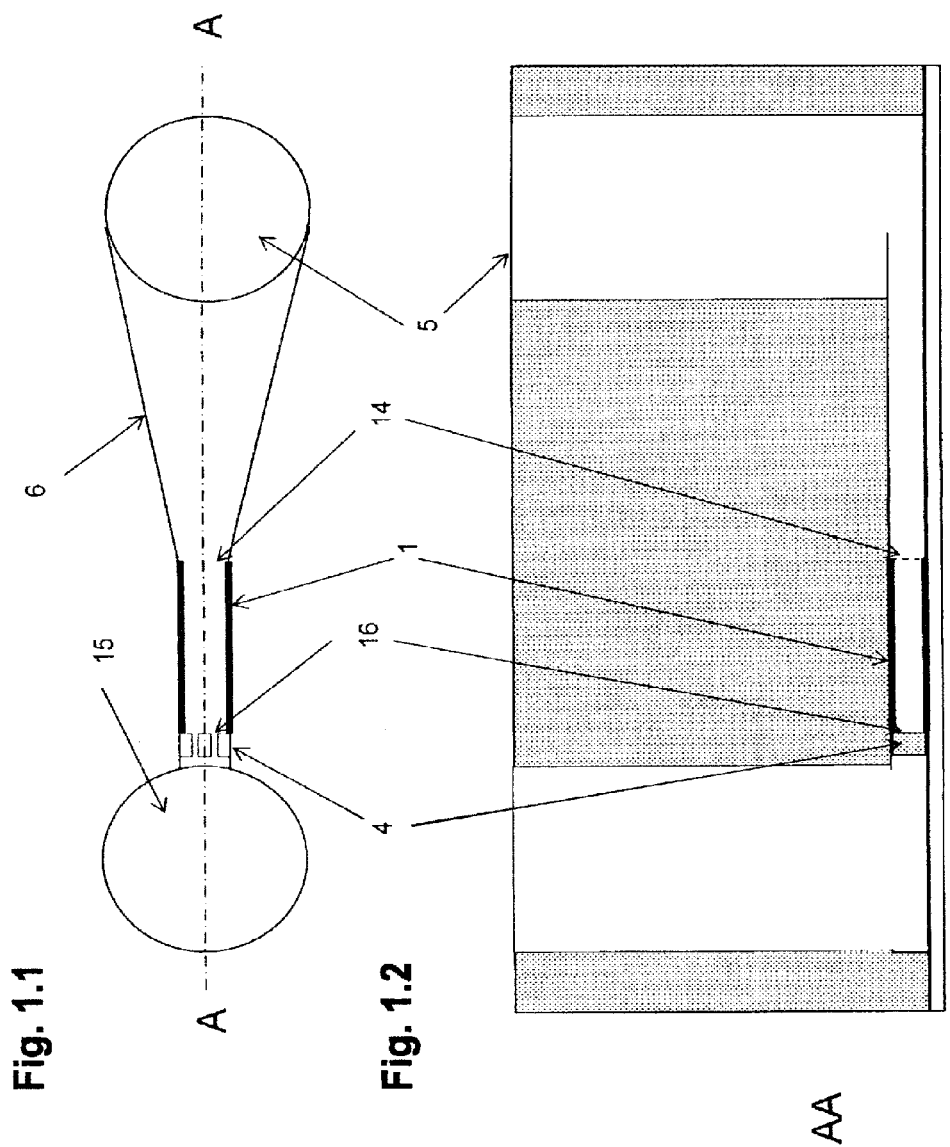
FIG. 1 depicts an exemplary embodiment of a microchannel 1 as reaction chamber (shown in bold) with its entry 14 that connects to an enlarged extremity 6 and to an inlet 5, its exit 16 that connects to a stopping means 4 (in the form of a filter structure) and to an outlet 15.

Within the scope of the present invention, the following definitions apply:

'Multiplexing' refers to the parallel performance of a number of assays, typically on a large number of compounds or molecules, with the ability to discriminate the results of each assay individually. These assays may e.g. be of biological and/or chemical nature and typically involve several target molecules to be detected and several capturing molecules to serve as agents to detect those target molecules. Said capturing molecules are typically attached as ligands on carrier substrates. The number of assays being conducted in parallel in a multiplexed assay is often referred to as the "level" of multiplexing and can range from just a few (2 or 3) to several hundreds of thousands for the higher levels of multiplexing. The latter are generally nucleic acid hybridization assays typically conducted today on microarrays, but which may be performed by the assay device disclosed herein.

'Single assay' refers to the performance of a single assay, where only one target molecule is sought to be detected by one capturing molecule.

'Reaction chamber' refers to a space where the biological and/or chemical reaction between a target molecule and a capturing molecule or ligand takes place.

'Microchannel' or 'microfluidic channel' refers to a closed channel, i.e. an elongated passage for fluids, with a cross-section microscopic in size, i.e. with the largest dimension (of the cross-section) being typically from 1 to 500 micrometers, preferably 10 to 500 micrometers, more preferably from 20 to 300 micrometers, even more preferably from 30 to 300 micrometers. A microchannel has a longitudinal direction, that is not necessarily a straight line, and that corresponds to the direction in which the fluids are directed within the microchannel, i.e. essentially to the direction corresponding to the vector addition of the speed vectors of a fluid passing in the microchannel, assuming a laminar flow regime. A microchannel has, at one end, an entry 14 and, at the other end, an exit 16, which are openings in the microchannel that e.g. let the fluids enter into the microchannel, respectively leave the microchannel. The cross-section of a microchannel is often constant throughout most of its length but this section can vary and may typically enlarge at least near the entry 14 or near the exit 16 in order to connect to an inlet 5, to an outlet 15, to one or more other microchannels or to another microfluidic component (such as a valve mechanism). A microchannel may extend so that the line formed by the longitudinal direction has any shape or length and may extend tridimensionally (i.e., the line formed by the extension in the longitudinal direction does not stay in a plane).

When referring to the "cross-section", the cross-section perpendicular to the longitudinal axis is meant.

The term "perimeter" refers to the internal perimeter of the microchannel or the circumference of the cross-section.

'Functionalized' refers to a particle or microparticle having one or more, but preferably one, ligand attached to its surface, which may serve as capturing or receptor molecule for a given target molecule (analyte). The term 'molecule' is to be understood broadly and may well include several molecules, particles or cells. For example, the target 'molecule' may be a virus particle and/or the capturing 'molecule' (ligand) may be a group of antigen-binding fragments. In another example, the target 'molecule' may be a nucleic acid such as a, DNA, a RNA or ssDNA fragment and the capturing 'molecule' another nucleic acid such as a DNA, RNA or ssDNA fragment that is designed to hybridize with the former. It may also be that for specifically capturing one target molecule different capturing molecules are necessary. Within the scope of the present invention, the mentioned examples will qualify as a 'capturing molecule' or 'target molecule', respectively. Ligands and target molecules may be natural, synthetic or semi-synthetic.

The term 'function' refers to the ability to bind and/or react with a given target molecule and does hence refer to the presence of a specific ligand.

The terms 'ligand', 'capturing molecule' and 'receptor molecule' are used herein synonymously. The same applies to the terms 'target molecule' and 'analyte', although the analyte may comprise several target molecules.

'Microparticles' refer to any type of particles microscopic in size, typically with the largest dimension being from 100 nm to 300 micrometers, preferably from 1 μm to 200 μm.

'Microcarriers' as used herein are microparticles which are functionalized in order to analyze and/or to react with an analyte in a sample. The term "functionalized microcarrier" is used simultaneously herein. When describing aspects that are not linked to their function, such as geometrical aspects or microfabrication aspects, 'Microcarriers' and 'Microparticles' can be considered equivalently herein.

A 'set' or 'set of microcarriers' refers to one or more microcarriers with the same functionalization. A set may be only one microcarrier or more than one microcarriers. The microcarriers of one set may carry more than one capturing molecules in order to capture two or more target molecules, but this is still referred to as one function. Two different sets of microcarriers, that are distinguishable from each other, may have the same functionalization.

The term 'biological readout' refers to the detection of whether or not a ligand attached to a microcarrier has bound or reacted with a target analyte. The biological readout may also provide quantitative information that is indicative of the amount of target analyte that has reacted.

A 'code' as used herein is any attribute or characteristic of a microparticle or microcarrier that is distinguishable upon observation or sensing and that is used to identify the microparticle or microcarrier or to associate the microparticle of microcarrier to a specific population (e.g. the population of microcarriers having a given function). A code on a microcarrier can be determined independently of its position and independently of the performance of an assay, i.e. it does not require the presence of a target analyte to be revealed. Typically, a code is characterized by the optical or magnetic response of the microparticle or microcarrier upon observation. This response might be defined for the microparticle or microcarrier as a whole (e.g. the color of the microcarrier) or might be spatially modulated in or on the microparticle or microcarrier to result in a patterned layout (e.g. a barcode obtained by the modulation of the color on the microcarrier). Examples of codes include but are not limited to color, shape, size, imprinted or engraved patterns, configuration of holes, holographic patterns, magnetic signatures, chemical composition, modification of light transmission or reflection characteristics, quantum dots emission or distinctive detectable foreign objects (e.g. oligonucleotide or other polymers) attached to the surface.

The term 'encoded microcarriers', respectively 'encoded microparticles' refers here to microcarriers, respectively microparticles that have a code. The microcarriers of the invention are individually encoded, i.e. each microcarrier carries its own code, even if several microcarriers (typically the microcarriers of one set) may carry a code with a same value (i.e. the microcarriers are not distinguishable based on their code alone). The different sets of encoded microcarriers of the invention can be distinguished and/or identified independently of the position of the microcarriers in the microchannel and independently of the performance of an assay.

Arranged "side by side" or standing "side by side" as used herein refers to a geometrical property that puts in relation the geometry of two or more microparticles with the geometry of the microchannel. The one or more microparticles are said to be arranged "side by side" at a given position in the microchannel when they (i) are in a configuration such as the two or more microparticles fit inside the microchannel and (ii) intersect the cross-section at that given position and (iii) their projected surfaces along the longitudinal direction (at that given position) do not overlap and are enclosed in the surface of the cross-section (at that given position). In general, in a microchannel that does not have a constant cross-section over its entire length, it is possible that one or more microparticles can be arranged side by side at some positions but not at other positions (although this general rule does not apply to the microchannel 1 of the invention which is required to be able to have microcarriers standing side by side over its entire length). Depending on the geometry of the microparticles, it is possible that two or more microparticles can stand side by side at a given position in the microchannel only when they are in certain orientations. When standing side by side, the microparticles may be in contact with each other or have a distance between them.

Figure 11:
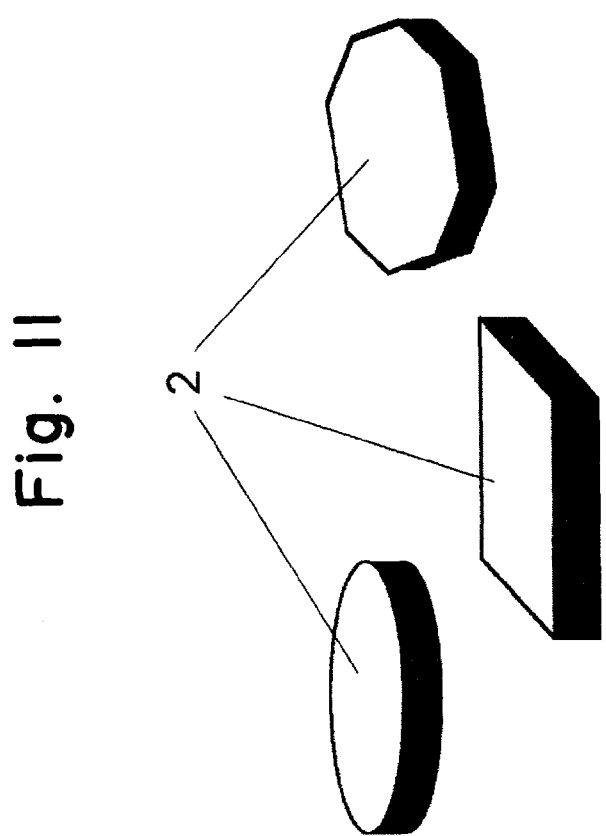
FIG. 11 illustrates various examples of microparticles with the form of a wafer. The front face has the form of a disk (left), of a quadrate (middle) or a hexagon (right).

The "form of a wafer" refers here to a particular shape of a microparticle where the height is notably smaller (e.g. by at least a factor of two) than both the width and the length and that microparticle has two essentially parallel and essentially flat surfaces (front faces) at the top and at the bottom (see FIG. 11). A "disk-like" shape refers to a shape in the form of a wafer with a circular front face.

The Microchannel

The microchannel 1 of the invention is preferably straight, i.e. the longitudinal direction extends along a straight line, but can also have a serpentine outline, i.e. the longitudinal direction extends to form a line with parallel tracks connected with arcs, to limit the footprint. The microchannel 1 is preferably essentially planar but may also extent tridimensionally.

The length of the microfluidic channel 1 can vary depending on its cross-section and on the desired footprint, generally to fit into the microfluidic chip 13 it is typically comprised in. Typically, it will range from 1 mm to 500 centimeters, preferably from 5 mm to 200 cm. The width and height of the microchannel is preferably from 500 nm to 300 micrometers. For example, a microchannel 1 with a serpentine outline and having a small cross-section (e.g. less than 100 microns), may achieve a relatively long length such as hundreds of centimeters in relatively small footprint (few square centimeters). For example, in one square centimeter it is possible to fit a 100 cm long serpentine microchannel 1 that has a 50 µm section (assuming that half the surface is occupied by the microchannel 1 and that the other half is spacing). In a much preferred embodiment, the microchannel 1 is substantially straight and has a length of 2 mm to 10 mm, a width from 200 microns to 600 mm and a height of 10 microns to 20 microns The microchannel 1 of the invention has an entry 14 and an exit 16 that let the fluids 9 enter, respectively leave the microchannel 1. The entry 14 is also used to introduce the microcarriers 2 inside the microchannel 1 and is typically connected to an inlet well 5, preferably via an enlarged extremity 6. The microchannel 1 of the invention preferably ends at a stopping means 4 as described below and is typically prolonged by another microfluidic channel (not serving as a reaction chamber) that conducts the fluids 9 to an outlet 15.

Figure 15:
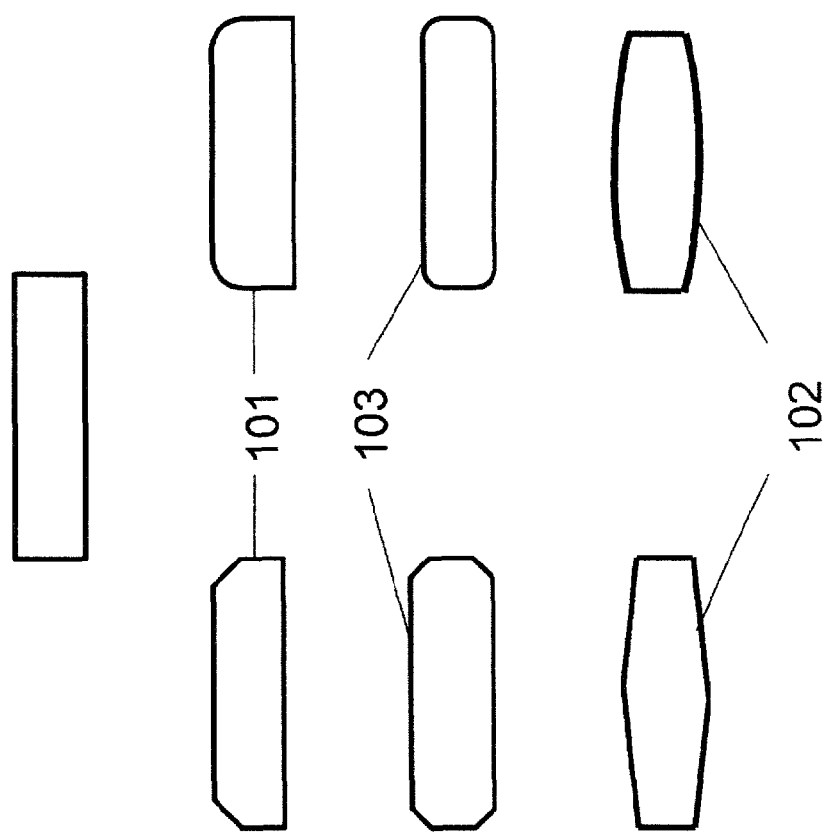
FIG. 15 depicts various non-limiting examples of forms that are rectangular or "close to rectangular". They illustrate preferred cross-sections for the microchannels 1 or for microcarriers 2 when they are in the form of a wafer.

The microchannel 1 has preferably a cross-section that is rectangular or close to rectangular (see FIG. 15), trapezoid or like a parallelogram. The microchannel has typically two lateral walls 101, a base 102 and a cover 103. The lateral walls are preferably, but not necessarily, straight and positioned in an angle close to 90 degrees to the base (bottom face) and the cover (top face), respectively. The lateral walls may be concavely or convexly curved or may connect to the base or the cover with an angle that is not straight for example 45 degrees or 60 degrees. Typically, the height of the microchannel is notably smaller (e.g. by at least a factor of two) than its width. In another embodiment, the base 102 and/or the cover 103 are slightly curved or structured with grooves or bumps, for example to facilitate the flow of fluids 9.

The microchannel 1 of the invention, which serves as a reaction chamber 1, is designed in such a way that it can contain at least two set of microcarriers 2 such as any two microcarriers 2 can stand side by side without touching each other and without touching the perimeter over its entire length, notably at its entry 14. In one embodiment, the microchannel 1 has at least one dimension of its cross-section that is larger than the sum of the largest extend of the largest projected surface of any two microcarriers 2. For example, in a microchannel 1 with a rectangular or close to rectangular cross-section and microcarriers 2 in the form of a wafer, said dimension may be the width of the microchannel 1 that is larger than the sum of the widths of any two microcarriers 2. Thus, the microchannel 1 may have a width such that two microparticles can be arranged side by side without inhibiting the movement of the microparticles in the longitudinal direction of the microchannel 1, e.g. during filling. More preferably, the width is such that the microparticles may pass each other without touching each other and without touching the perimeter of the microchannel 1 which due to friction may also lead to blocking. In a preferred embodiment, the cross-section of the microchannel 1 is preferably constant or essentially constant over the entire length of the microchannel 1. In another embodiment, the microchannel 1 is connected to an enlarged extremity 6, where the cross-section widens, typically at the entry 14, to ease the introduction of the microcarriers. In a preferred embodiment, the enlarged extremity 6 at the entry 14 of a rectangular or essentially rectangular microchannel is done by increasing the distance of the lateral walls 101 to the longitudinal axis increases while the height of the microchannel (i.e. the distance between base and cover) preferably remains essentially constant.

In a preferred embodiment, the microchannel 1 is made of or comprises silicon, SU-8 (an epoxy based photoresist), polyimide (PI), polydimethylsiloxane (PDMS), silicone, or other thermoplastic elastomers (TPE), polymethylmethacrylate (PMMA), Teflon (PTFE), thermoplastic elastomers (TPE), Victrex PEEK™, Polycarbonate, Polyvinyl chloride (PVC), polypropylene (PP), polyethylene (PE), polystyrene (PS), Fluorinated Ethylene-Propylene (FEP), Cyclic Olefin (Co)polymer (COP or COC) or other thermoplastic polymers, quartz, glass or plateable metals such as nickel, silver or gold, most preferably of transparent polymers. Most preferably, the microchannel is made of Cyclic Olefin (Co)polymer.

Preferably, the microchannel 1 is transparent on at least one side. Thereby, the microparticles can be readily observed via an according means for optical inspection, e.g. a microscope. This allows for an easy identification of the sets of microcarriers 2 that are encoded with optical techniques when they are placed within the microchannel 1 and determination of the biological readout by conventional techniques based on optical response used in the art for that determination. Suitable materials for providing transparency are e.g. SU-8, PDMS or silicone.

The microchannel 1 can be fabricated using conventional photolithography and/or stamping and/or injection molding techniques that are extensively described in the literature (e.g. Fundamentals of microfabrication by Marc J. Madou, ISBN: 0849308267, 9780849308260, Fundamentals and Applications of Microfluidics by Nam-Trung Nguyen and Steve Wereley, ISBN: 9781580533430, chapter 3). For example, the microchannel 1 may be produced by etching a channel into a substrate by known methods and then sealing it with either a plate e.g. made of glass or a second channel which was also etched into a substrate. The microfabrication techniques can also be used to produce microparticles, for example for producing silicon microparticles on a wafer as described in EP1276555B1.

At the scales that are considered, the flows are laminar. In order to ensure that the target molecules of interest in the sample pass in the proximity of a maximum of microcarriers 2, the microchannel 1 should be designed in such a way that the microcarriers 2 let open a section as small as possible around them which allows the sample 9 to flow through. The flowrate will e.g. be limited by the section left open around the microcarriers, by the length of the microchannel, by the forces that move the fluids (e.g. the pressure that is applied) and by the fluidic properties of the sample (viscosity, size of molecules the sample carries, etc.).

Microcarriers and Sets of Microcarriers

The microchannel 1 holds simultaneously at least two sets of microcarriers 2, but may also comprise three, four, five, ten or hundreds or more sets of microcarriers. For higher levels of multiplexing (for example for nucleic acid hybridization assays) the microchannel may contain hundreds of thousands of sets. This is e.g. achievable with long and wide microchannels 1 coupled with small microcarriers 2.

Sizes, shapes and material as well as the distinction between microparticles and microcarriers are outlined in the definition section.

The microparticles or microcarriers 2 of the invention may be made from or comprise any material routinely used in high-throughput screening technology and diagnostics. Non-limiting examples of these materials include latex, polystyrene, cross-linked dextrans, polymethylstyrene, polycarbonate, polypropylene, cellulose, polyacrylamide, polydimethylacrylamide, fluorinated ethylene-propylene as well as materials commonly used in microfabrication or micromilling such as glass, $SiO_2$, silicon, PMMA (polymethylmethacrylate), gold, silver, aluminium, steel or other metals or epoxy-based photosensitive materials such as SU-8. The microparticles may be of any shapes and sizes. Preferably, the microcarriers 2 are made of silicon.

The microcarriers 2 of the invention are encoded in such a way that their function can be determined by reading the code.

The microparticles and the microcarriers 2 have preferably a spherical shape or the form of a wafer which means that their height is notably smaller (e.g. by at least a factor of two) than both their width and their length and that they have two essentially parallel and essentially flat surfaces (front faces) at the top and at the bottom.

Figure 12:
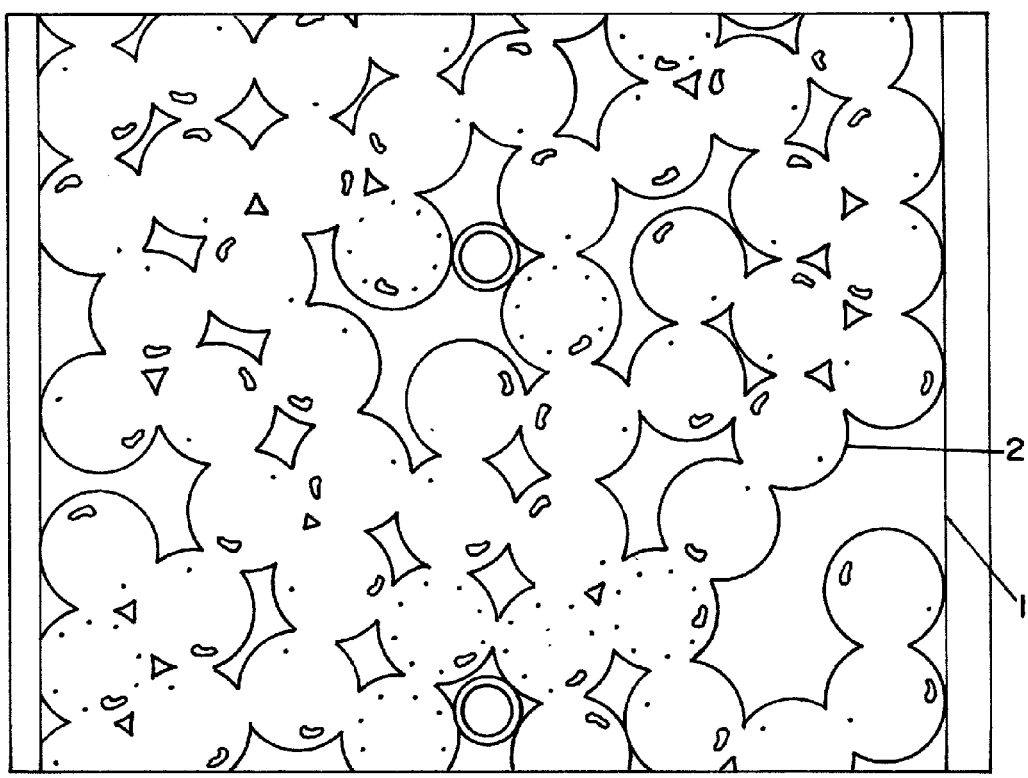
FIG. 12 shows an exemplary embodiment where the microcarriers 2 have a disk-like shape and are encoded with a pattern of traversing holes 21 and an L-shaped orientation mark 20. This figure shows a line drawing of a bright field (white light) picture of the microcarriers taken after flowing the sample 9. A fluorescent picture will expose the microcarriers that have reacted after flowing the sample 9.
Figure 13:
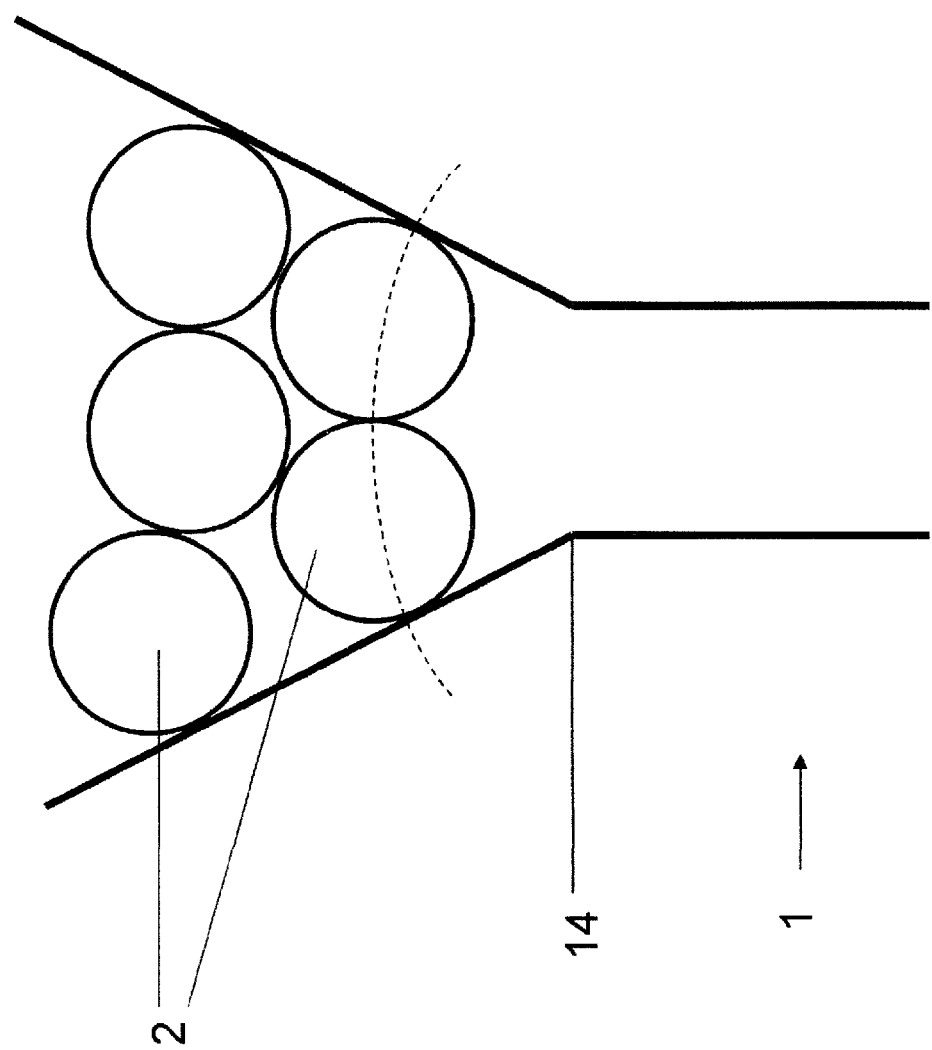
FIG. 13 shows how arches can form in a funnel that guides the microcarriers 2 into a narrow microchannel 1 and therefore clog the entry 14 of the microchannel 1.
Figure 14:
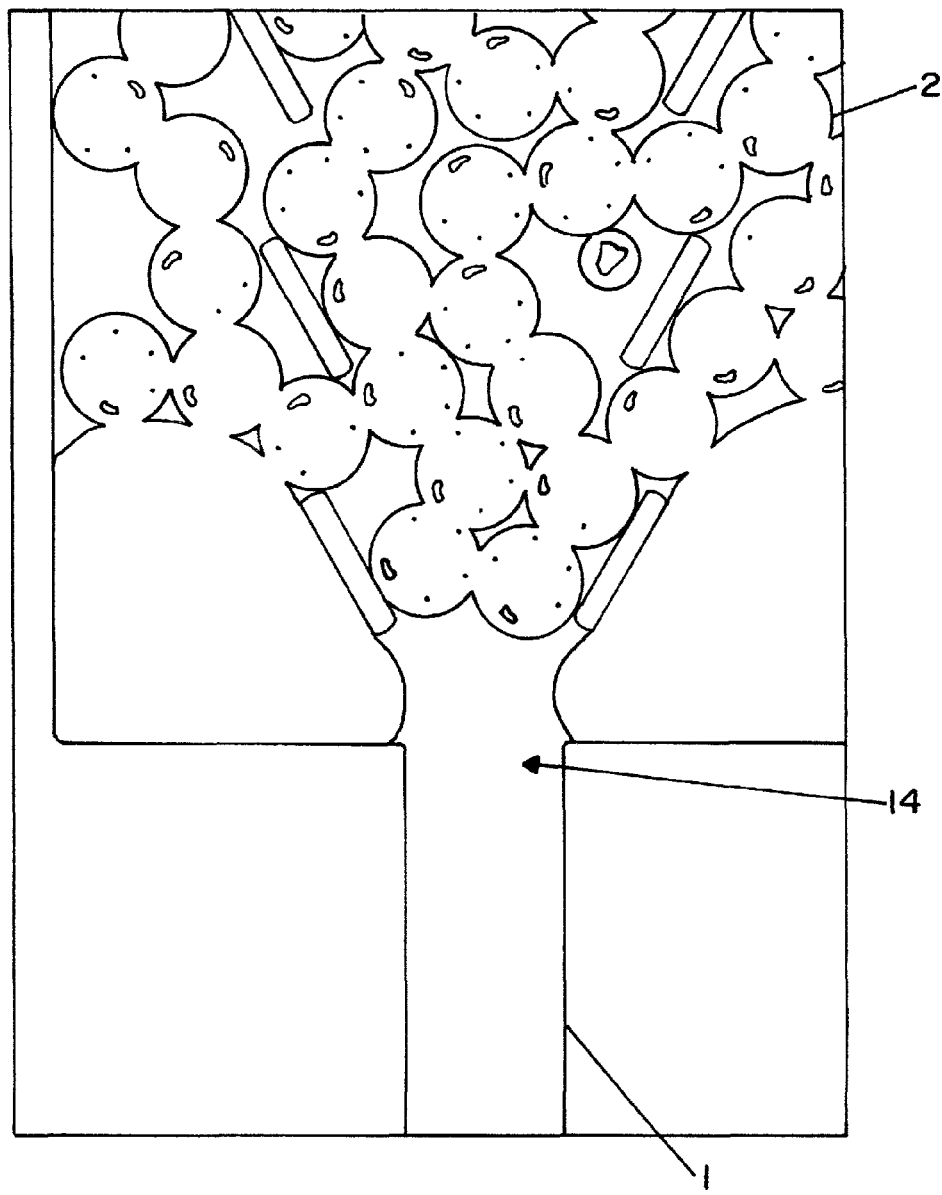
FIG. 14 shows a line drawing of a picture of an arc of microcarriers 2 being formed in a funnelling construct, which clogs the entry of a microchannel 1.

Thus, when the microcarriers 2 with the form of a wafer are introduced in a microchannel 1 with a rectangular or close to rectangular section as described above, they lay flat on either of their front faces and they can be easily detected by optical means. FIG. 12 shows exemplary embodiments of wafer shaped microcarriers 2. The major surface can have any shape; non limiting examples are a square, a rectangle, a circle, a triangle or a hexagon (FIG. 11, right).

In a preferred embodiment, the microcarriers 2 have a disk-like shape with the front face in form of a circle, and are encoded by a pattern of traversing holes 21, which preferably also include an asymmetric orientation mark 20 such as a triangle or an L-shaped sign. This combination of code and shape allows for an easy identification through imaging decoding techniques.

In another embodiment, the microcarriers 2 have magnetic properties which are e.g. suitable to immobilize them within the microchannel. The microcarriers 2 of each set are typically functionalized identically.

The microcarriers 2 may well have different sizes and shapes in relation to each other. The microcarriers 2 are encoded so that the various sets are distinguishable from each other by at least one attribute or characteristic that is observable, i.e. the code. Although all the microcarriers 2 are individually encoded, the microcarriers 2 of a given set preferably share a same code. As encoded microcarriers 2 are used, they may be introduced in random sequence rather than in a controlled manner.

The microcarriers 2 serve as supports for chemical and biological assays. In this capacity, the microcarriers 2 may contain one or more ligands attached to their surface and may be contacted with target analytes to determine the presence or absence of particular analytes of interest, or they may serve as supports for combinatorial chemistry reactions performed on the attached ligand. In a preferred embodiment, each microcarrier has one ligand attached to its surface. It is to be understood that the term one 'ligand' as used herein is not meant to refer numerically to one molecule only but to one type of ligand. A large spectrum of chemical and biological functionalities may be attached as ligands to the microparticles of the invention, including antibodies and other proteins as well as nucleic acids such as DNA, RNA or ssDNA fragments or aptamers designed to bind to specific molecules of interest. These functionalities include all functionalities that are routinely used in high-throughput screening technology and diagnostics. Furthermore, the microcarriers 2 can be functionalized in a variety of ways to allow attachment of an initial reactant. Examples of target analytes for the ligands attached to the microcarriers 2 include antigens, antibodies, receptors, haptens, enzymes, proteins, peptides, nucleic acids, drugs, hormones, pathogens, toxins, cells or any other chemicals or molecules of interest.

Means to Restrict the Longitudinal Movement of the Microcarriers

The invention provides a means to increase the speed of the flow relative to that of the microcarriers 2 in order to improve the chances of contact between molecules of interest 3 in the fluid 9 and the receptors 8 attached to the microcarriers 2. It is therefore important to restrict the movement of the microcarriers 2 in the direction of the flow, which is in the longitudinal direction while still letting the fluids 9 flow through. The presence of a restriction means provides an essentially static configuration for performing the assay and readout in the same place enabling kinetic readout in addition to faster mass transfer. The motion of microcarriers 2 perpendicular to the flow can occur and may even have a positive impact on the speed of mass transfer, if the motion of the microcarriers 2 is rapid enough, because it increases the virtual size of the capturing surface (this is a form of agitation that can be achieved, for example, through tapping, vibration or sonication).

The restriction of the longitudinal movement of the microcarriers can be done in several ways. For example, at least one stopping means 4 that lets fluids 9 flow through but blocks the passage of the microparticles 2 can be used at the end of the reaction chamber 1. Non limiting examples of said stopping means 4 include a grid, a wire, a mesh filter, a weir construct, one or more pillars, a reduction of the section of the microchannel, electrostatic forces, in particular one or more microparticles retained using electrostatic forces, dielectrophoretic forces, in particular one or more microparticles retained using dielectrophoretic forces, a magnetic particle, etc. Solutions based on partial compression of non-rigid microchannels 1 (i.e. contracting the geometry of the microchannel, e.g. in the case of microchannels made of soft polymer such as PDMS or paraffin) may also be used as stopping means 4. The stopping means 4 may be fixed or removable. Removable stopping means, e.g. magnetic particles, allow an easy removal of the microparticles 2 in direction of the flow 9 for microparticles replacement or microparticles analysis. Fixed stopping means 4, such as a grid, may be removed by a laser for removing the microparticles 2, e.g. for analyzing them.

Alternatively or additionally, if the microcarriers 2 have magnetic properties, the microcarriers 2 can be immobilized by applying a magnetic field. Hence, the presence of a stopping means 4 may not be necessary. In an alternative embodiment, the microcarriers 2 are immobilized by using dielectrophoretic forces.

Thanks to the restricted movement of the microcarriers, the setup also facilitates washing steps, the flushing of additional reagents as well as biological readout, which is preferably done in a static mode.

Design of the Microchannel in Relation to the Microcarriers

According to the present invention, the microchannel 1 has a cross-section that allows at least two of any of the microcarriers 2 to be arranged side by side over the entire length of the microchannel 1, notably at the entry 14, without touching each other and without touching the perimeter. Note that, strictly speaking, the microchannel 1 of the invention, which serves as a reaction chamber 1, ends at any stopping means that might be built in the microchannel (e.g. a filter or mesh structure or the reduction of the section, etc.). This means that any microfluidic portion that contains a stopping means 4 is not considered part of the microchannel 1 of the invention and is therefore not required to allow two or more microcarriers 2 to stand side by side. For clarity, when a microchannel continues after the stopping means 4, this part is considered as another microchannel (not serving as a reaction chamber) connected to the microchannel 1 of the invention (which serves as a reaction chamber), for example to allow the fluids to leave via an outlet (see FIG. 1).

The fact that the cross-section of the microchannel 1 and the shape of the microcarriers 2 allows for at least two microcarriers to stand side by side without touching each other and without touching the perimeter does not mean that they must not touch each other or touch the perimeter. It just means that the respective geometries of the microchannel 1 and the microcarriers 2 do not force the microcarriers 2 to touch each other or the perimeter when they stand side by side, although they might still do so when they move freely inside the microchannel 1 or as they settle after having their longitudinal movement restricted.

The ability to stand side by side without touching each other and without touching the perimeter of the microchannel 1 means that the microcarriers 2 can pass each other if they move at different speeds in the longitudinal direction of the microchannel 1, without being subject to friction against the walls of the microchannel 1 or against each other. This configuration decreases chances of clogging the entry 14 to the microchannel 1 since it is much more difficult to form arches when two microcarriers 2 can stand side by side at the entry 14 and notably more difficult in preferred embodiments where more than two microcarriers are allowed to stand side by side. It also allows microcarriers 2 to pass each other should one of them be clocked by an obstacle. Obstacles can be debris that would be present in the microchannel 1, for example when the method is performed in a research laboratory environment (as opposed to a controlled factory environment) just before performing an assay. Obstacles can also be constructs, such as pillars, that are built in the microfluidic channel 1 for facilitating the fabrication of the microchannel 1 or to ensure its rigidity, for example in case of microchannels build using soft polymers such as PDMS, Taping the device that comprises the microfluidic channel 1 also helps during the introduction of the microcarriers 2. When heavier microparticles are used, such as silicon microparticles, the taping is more efficient when it is done at low frequencies, typically below 5 Hertz.

In a more preferred embodiment, more than two microcarriers 2 can be arranged side by side in the microchannel 1 in order to reduce even more the sensitivity to obstacles (e.g. dusts) or arches formation, typically from 3 (three) to 50 (fifty) microcarriers, more preferably from 3 (three) to 12 (twelve).

In preferred embodiments, the microcarriers 2 have a shape that minimizes the contact surface between them when they are in the microchannel 1 to reduce friction. Typically, shapes with curved surfaces, such as spheres or disk-like shapes, are preferred compared to edged surfaces (such cubical or polygonal shapes).

In a preferred embodiment, the microcarriers 2 have a disk-like shape that offers the additional benefit of being easily identifiable in an image. Other shapes that present curved surfaces that can contact with other microcarriers 2 can also be considered, such as microcarriers 2 in the form of a wafer with a front face that has an oval, ellipsoid or close to circular shape.

The Monolayer Arrangement

In much preferred embodiment, the shape of the microcarriers 2 and the cross-section of the microchannel 1 are chosen such that the microcarriers 2 form a monolayer arrangement and let open a minimum section around them for the sample 9 to flow through. "Monolayer arrangement" as used herein refers to a spatial configuration where there exists a point from where all the microcarriers 2 can be observed in direct line without hiding or occluding each other any part that is essential for their identification (i.e. to determine the code). In the case of a microchannel 1 that is lying flat (i.e. with a longitudinal direction that extends essentially horizontally) this translates into the inability of the microcarriers 2 to go on top of each other or to overlap when they are inside the microchannel 1. Provided that the microchannel 1 is transparent on at least one side, the monolayer arrangement is much preferred as it will facilitate biological readout and microcarriers' identification by simple optical means directly inside the reaction chamber 1.

Figure 4:
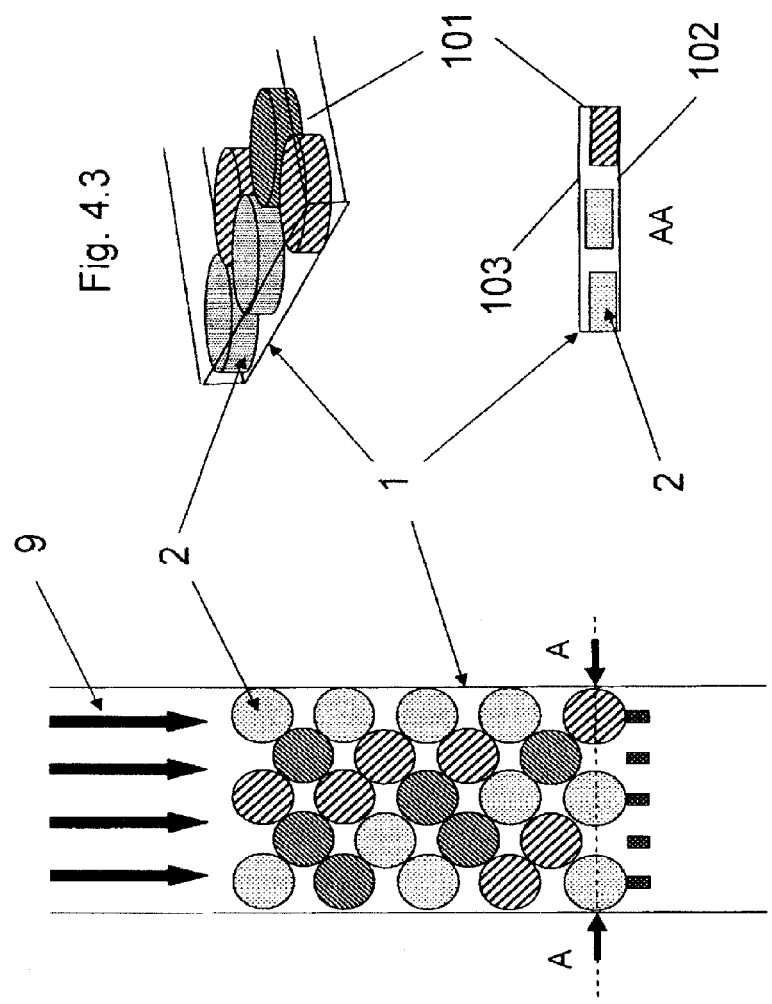
FIG. 4 shows an exemplary embodiment where the microcarriers 2 have a disk-like shape (i.e. a shape in the form of a wafer with a circular front face) and are in a microchannel 1 with a rectangular cross-section. The microchannel 1 has two lateral walls 101, a base 102 and a cover 103. The cross-section of the microchannel 1 is such that the microcarriers 2 form a monolayer arrangement and have their rotational movements restricted.

Combined with the fact that at least two microcarriers 2 can be side by side as provided by the invention, this configuration forms a quasi-two dimensional monolayer arrangement while still minimizing the section around the microchannels for the sample 9 to flow through (see e.g. FIG. 4). As illustrated in FIG. 4.2, this does not necessarily involve a strict alignment of the microcarriers 2 in a single plane. Preferably more than two microcarriers 2 are allowed to be positioned side by side, typically from 3 (three) to 50 (fifty) microcarriers 2, more preferably from 3 (three) to 12 (twelve). This arrangement will consume more sample fluid 9 than the strict alignment of the microcarriers 2 one behind each other as seen in the prior art but will be much easier to prepare.

Preferably, the section of the microchannel 1 is constant in the area where the reaction occurs in the microcarriers 2 in order to facilitate the uniformity of the flow conditions.

Microcarriers' Orientation and Identification

When working with encoded microcarriers 2 in conjunction with the monolayer arrangement, it is further advantageous to choose the shape of the microcarriers 2, the shape and material of the microchannel 1 and the decoding mechanism in such a way that the codes can be read without having to actively manipulate the microcarriers 2 to position and/or orient them appropriately when observing them directly in the microchannel 1. This can be achieved, for example, by using encoding mechanisms that do not require any particular orientation or position, such as the size or color of the entire microcarrier 2 which can be, for example, spherical (thus not requiring any particular orientation).

Alternatively, the shape of the microcarriers may be such that their rotation is passively restricted, i.e. restricted without requiring any external forces other than those resulting from the geometrical constraints, when inside the microchannel 1 so that any code is appropriately presented to an observation/sensing device.

Figure 8:
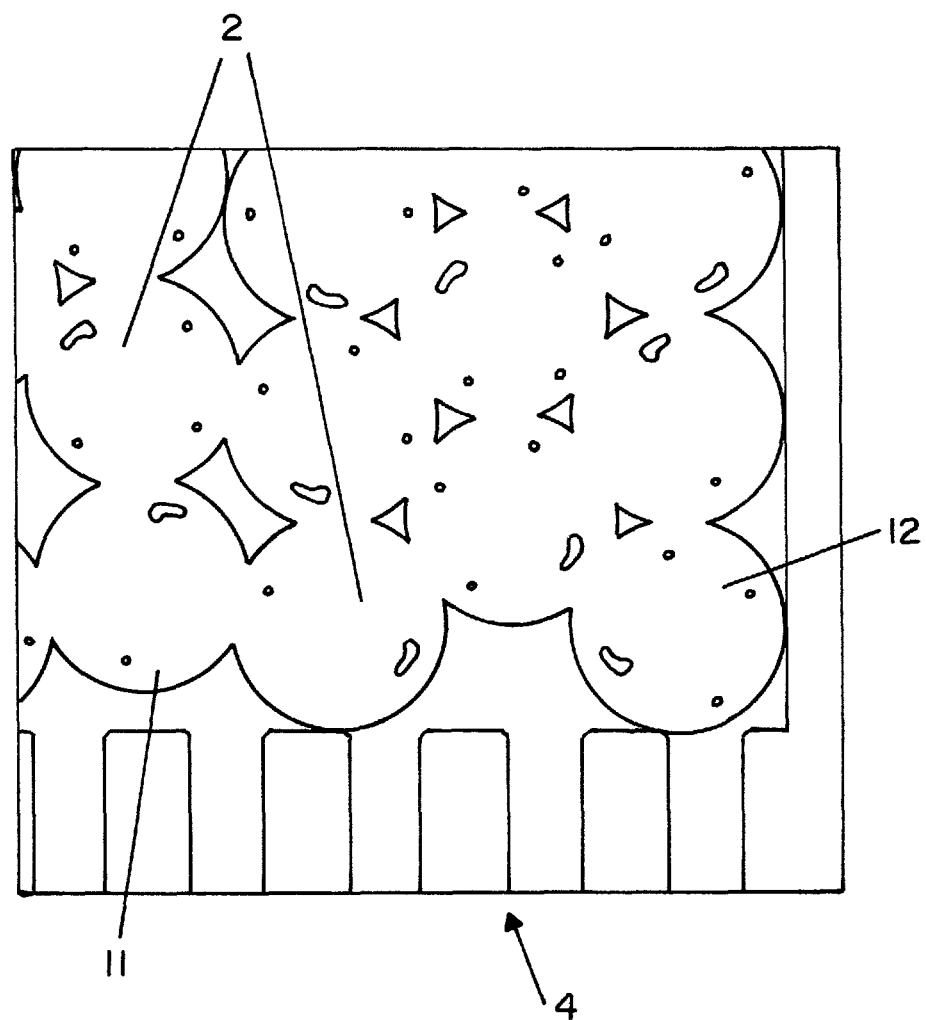
FIG. 8 shows a line drawing of an image taken by a CCD camera in connection with biological readout of microcarriers 2 in a simple multiplex assay. Two sets of microcarriers 2 were introduced in the microchannel: a first set of microcarriers 11 (code with one hole) functionalized with a DNA probe P1(5'-CAA CCC CAG CTA ATA TTA TT-3') (SEQ ID NO: 1) and a second set of microcarriers 12 (code with three holes) functionalized with another DNA probe P2 (5'-TGG GTA AGT TAG GGC GAT GG-3') (SEQ ID NO: 2). A solution containing fluorescently labeled DNA target T1 (5' Cy5-AAT AAT ATT AGC TGG GGT TG-3') (SEQ ID NO: 3) complementary with probe P1 was then flushed and only the microcarriers 11 functionalized with the DNA probe P1 reacted.

An exemplary embodiment of this concept is to design microcarriers 2 with the form of a wafer having a code present on one or both faces and bring them inside a microchannel 1 with a rectangular or close to rectangular cross-section which is preferably made of transparent material (see FIG. 8) on at least either the base 102 or the cover 103. The height of the microchannel 1 is preferably less than the height of two microcarriers, having the effect that the microcarriers 2 cannot go on top of each other. This way, the microcarriers form a monolayer arrangement and can only be upside-down but always essentially present one of the flat surfaces to any sensing device that is placed to observe the plane of the microchannel 1 (as in FIG. 5). This additional constraint on the shape of the microcarriers 2 does actually not make their loading much more difficult when done through a vertical inlet 5 with a fluid 9 being sucked into the microchannel 1 (as depicted in FIGS. 2 and 3) thanks to the use of a microchannel 1 that is relatively wide compared to the size of the microcarrier 2, as provided by the invention. Exemplary embodiments of such a microchannel 1 can be seen in FIGS. 4 to 6.

If any code is present on a face of the microcarriers 2 it is easily observable for all the microcarriers that have the right face presented to the device (statistically half of them). Furthermore, if the code is present on or visible from both sides, then all the microcarriers 2 can be decoded without needing any further active manipulation to orient them.

Figure 7:
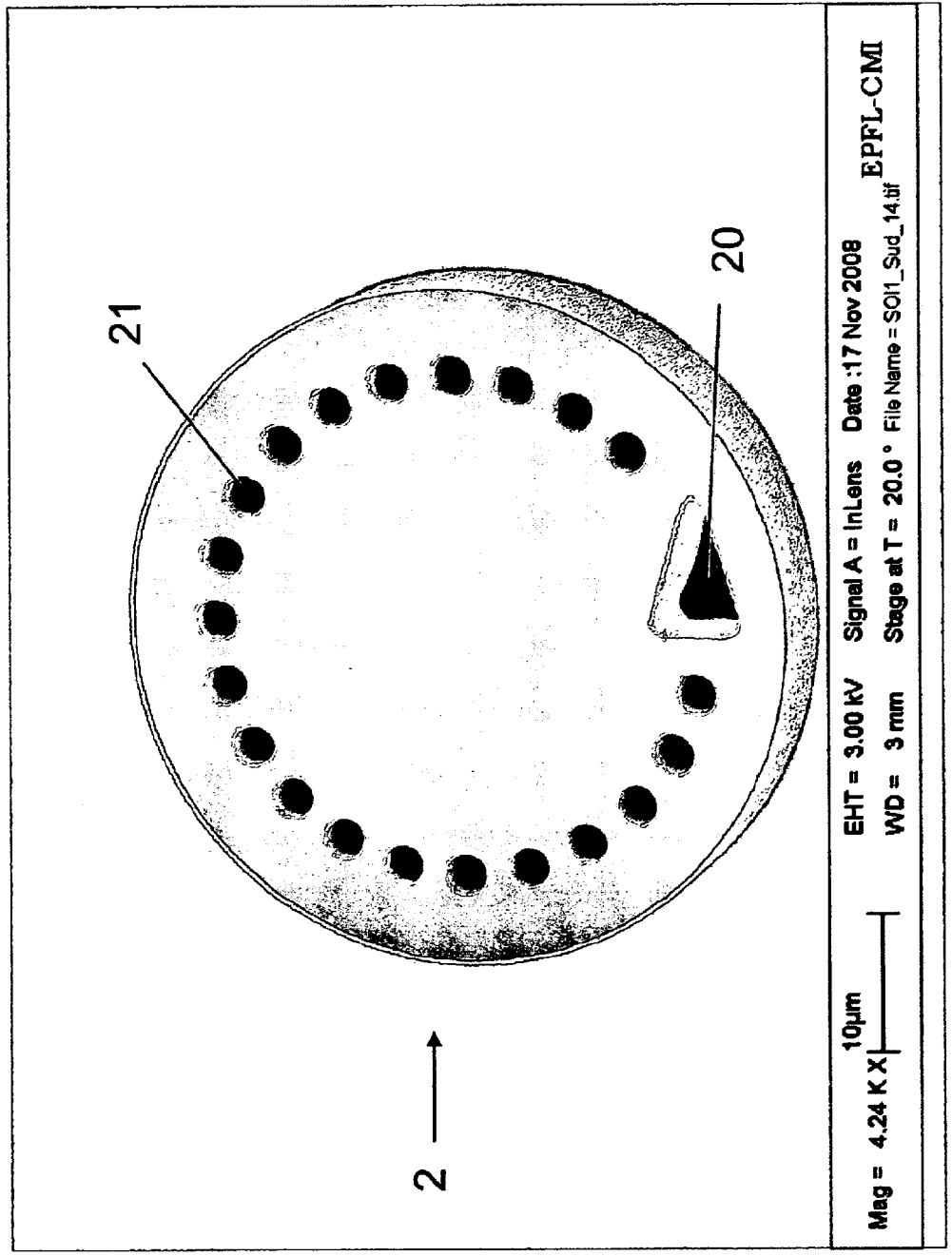
FIG. 7 shows an exemplary embodiment of a microcarrier 2 having a disk-like shape and a code in the form of a pattern of traversing holes 21 through the microcarrier 2. The microcarrier 2 exhibits a triangle orientation mark 20 that is used to determine if the microcarrier 2 is upside-down and also serves as the starting point of the code pattern. The microcarrier 2 has the coding elements on the periphery thus leaving a significant portion, around the center of the microcarrier 2, of the surface for a dedicated uniform and flat region suitable for biological readout. Encoded microcarriers 2 having a disk-like shape (as described above) may be located in a microchannel 1 with a rectangular cross-section. The cross-section of the microchannel 1 is such that the microcarriers 2 form a monolayer arrangement (they cannot go on top of each other) and have their rotational movements restricted so that they lay essentially flat inside the microchannel.

A preferred embodiment of this concept consists in using codes that traverse the microcarriers 2 so that the code can be read and interpreted from both sides. Note that, if the coding scheme is patterned (as opposed to being a non localized characteristic of the entire face, such as color, size, etc.), it may need to be combined with a mark that indicates orientation (i.e. a mark with an asymmetry such as an L-shaped mark or a triangle). FIG. 7 shows a picture of an exemplary embodiment of such a code created by using traversing holes 21 on a microcarrier in the form of a wafer (a disk-like microcarrier in the figure). Said encoding scheme further allows identifying the microcarriers independently from the performance of an assay and independently of their position within the microchannel.

Figure 5:
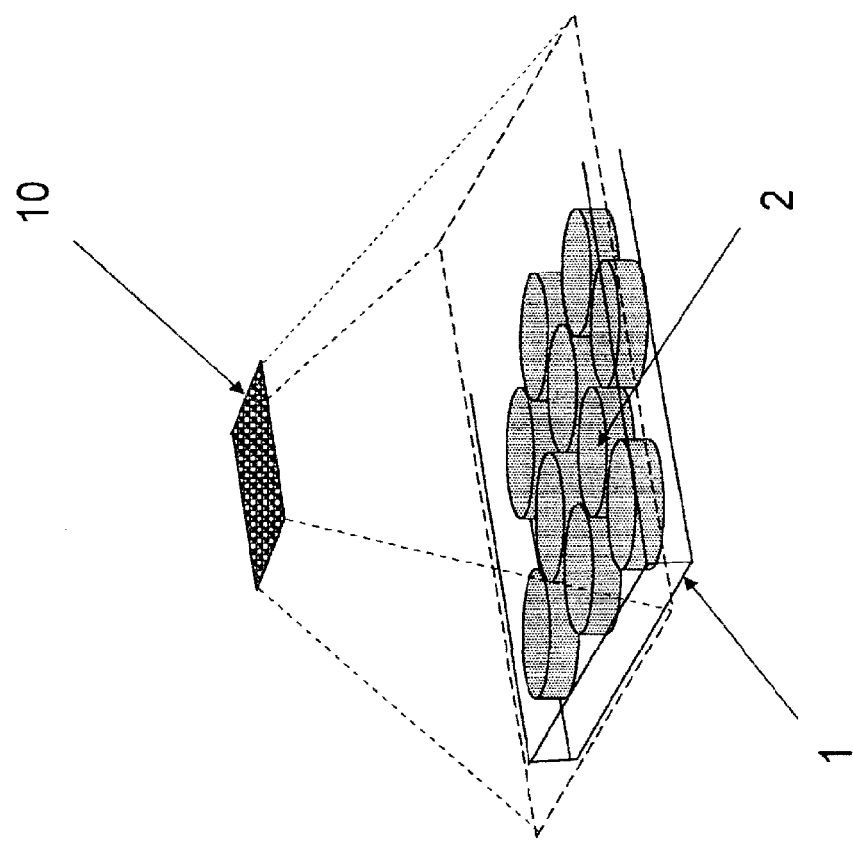
FIG. 5 illustrates the use of an array-type of sensor 10, e.g. a CCD or a C-MOS photo-sensor, to capture a wide field image of the monolayer arrangement of microcarriers 2 inside the microfluidic channel 1.
Figure 6:
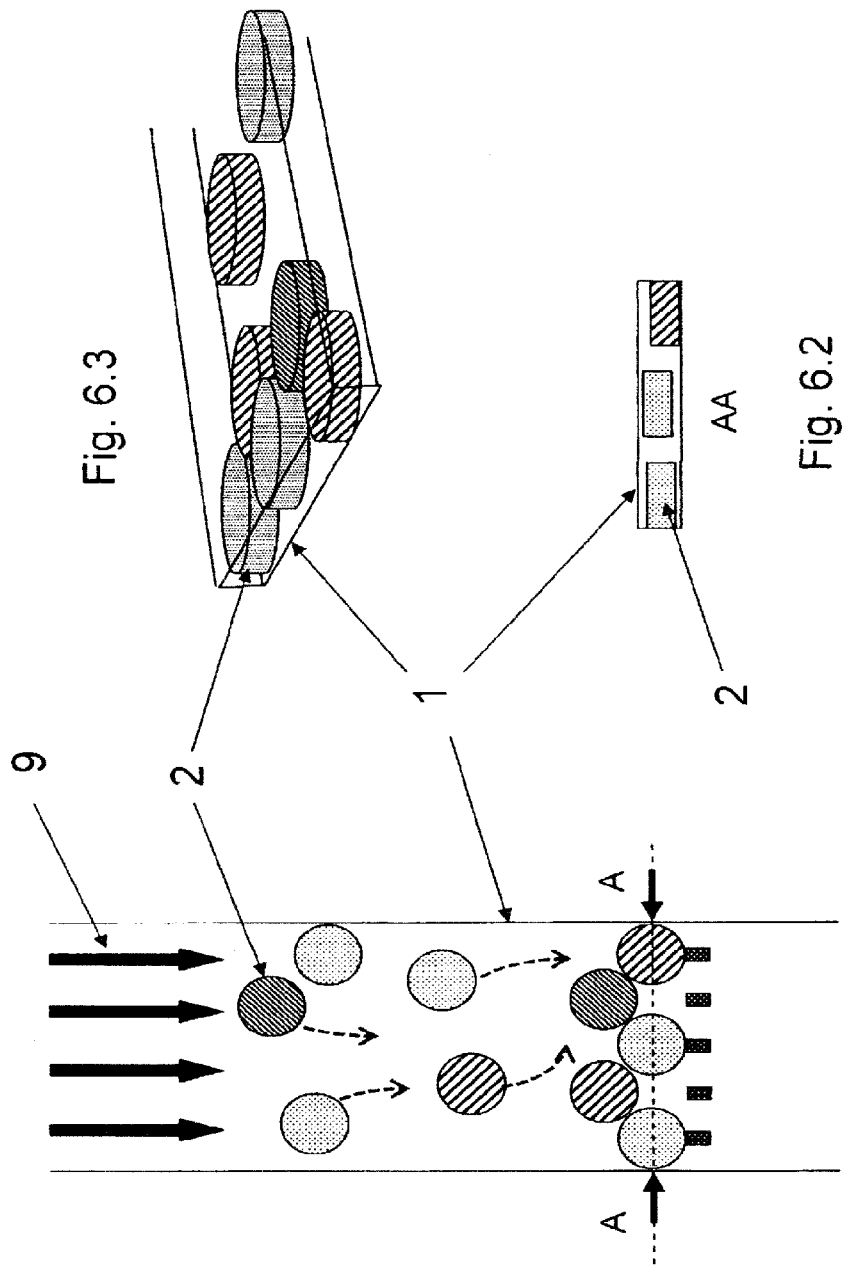
FIG. 6 shows an exemplary embodiment where the microcarriers 2 have a disk-like shape and are in a microchannel 1 with a rectangular cross-section. It illustrates how the microcarriers can have relatively free motion (in a 2D plane in this example) until they reach the point where their longitudinal movement is restricted. This allows them to pass each other and reduces the risk of blocking a large number of microcarriers in case of presence of an obstacle.

Since the orientation and the position of the microcarriers 2 in the plane is not controlled, the preferred method for detecting and decoding said wafer-shaped microcarriers 2 is to capture an image or several images of the reaction chamber 1 using an array type of sensor (e.g. a CCD or C-MOS photosensor array) such as illustrated in FIG. 5 or a fast scanning system that constructs the image and then perform an analytical operation on the image in order to detect the position of the microcarrier 2 and interpret their code. This analytical operation typically includes a shape recognition algorithm such as the Hough algorithm to detect the position of the microcarriers 2 and a "virtually rotation" of the microcarrier 2 in order to interpret their code independently of their orientation. The analytical operation on the image is also typically able to reduce or eliminate the effect of presence of debris or air bubbles in the reaction chamber 1, A "picture" taken by a CCD (or C-MOS) camera with a microscope can be used to detect and decode such microcarriers 2 and this same camera can also be used to read the fluorescent signal for biological readout.

Introduction of Microcarriers into the Microchannel

The microchannel 1 of the invention has en entry 14 that allows introducing the microcarriers 2 inside the microchannel 1. A classical method for introducing the microparticles 2 into the microchannel 1 is to have them in a suspension in a buffer solution which is flown via an inlet 5, connected to the entry 14, into the microchannel 1.

The microchannel 1 has preferably, next to its entry 14, an enlarged section 6 connected to one or more vertical wells 7 which serve as inlet 5 for introducing the microparticles 2 into the microchannel 1 (see FIG. 2, 3). The enlarged section 6 forms a funnel that allows guiding the microcarriers 2 and the fluids 9 from the inlet 5 into the microchannel 1.

As explained above, the microchannel 1 of the invention has a cross-section relative to the shape of the microcarriers 2 that allows having at least two microcarriers 2 standing side by side in the microchannel 1 over its entire length, particularly at the entry 14, thereby reducing the chances of clogging the entry 14 by forming arches.

A common problem that is encountered when introducing microparticles 2 in suspension into microchannels 1 is that, when the flow 9 stops (for example when switching from one solution to another), the remaining microparticles 2 tend to sediment at the bottom of the well 7, possibly in areas where they can get caught in laminar vortexes 8 (see FIG. 3). This makes them difficult to move in a controlled manner and increases the risk that different sets of microcarriers 2 are mixed, which is of no consequence if the microcarriers 2 are individually encoded but would be problematic if the microcarriers 2 of each set need to be introduced in a controlled manner in the microchannel 1 such as required by the existing art. Typically, time is given to the microparticles 2 to fully settle down and lie on the bottom of the inlet 5. They are then moved into the microchannel 1 under the combined actions of the aspiration of the buffer solution and of gravity forces acting on the microparticles 2 by tilting the device. This method is particularly effective for heavy microparticles 2 such as silicon microparticles. Agitation and shaking can further help the process.

In order to overcome the problem of microparticles 2 that settle in places where they cannot be removed, in an embodiment of the invention, besides the well 7 a second well T used as an inlet 5' for a rinsing flow 9' is present. Thereby, a continuous (or micro-pulsed) rinsing flow 9' streaming through the microchannel 1 can be achieved while introducing the microparticles 2 to prevent sedimentation of that latter (see FIG. 2). When the microparticles 2 are heavy, such as made of silicon, this is generally not required as the gravity forces acting on the microparticules 2 by tilting the device is sufficient to move them in the desired direction.

It is also advised to flush a clean fluid 9 (i.e. without microparticles in suspension) in the microparticles inlet 5 after the introduction of microparticles in order to ensure that no particles are left in the well 7 or in the enlarged extremity 6 of the microchannel 1. This can also be combined with an optical inspection of the enlarged extremity 6 of the microchannel 1 to further increase the reliability of the procedure.

Method

In a second aspect, the invention provides a method for performing a multiplexed assay based on microcarriers comprising the steps of a) providing an assay device comprising of a microchannel 1 as reaction chamber and providing at least two sets of encoded microcarriers 2, wherein the code of said microcarriers 2 is indicative of the function and wherein the shape and size of said microcarriers 2 relative to the cross-section of said microchannel 1 allows to have, over the entire length of said microchannel 1, at least two of any of said microcarriers 2 standing side by side;

b) at least partially filling said microchannel 1 with said at least two sets of encoded microcarriers 2;

c) restricting the movement of said microcarriers 2 in the longitudinal direction of said microchannel 1 while still letting the fluids 9 flow through;

d) flowing a sample potentially comprising one or more target molecules 3 through said microchannel 1 comprising said microcarriers 2;

e) identifying the sets of microcarriers 2; and f) detecting a reaction between the ligand and the target molecule, i.e. performing a biological readout, and correlating the presence or absence of a reaction with the identity of a specific set to infer the presence or absence of a target molecule 3 in the sample. This typically correlates with the identification of the microcarriers 2.

The microchannel 1, the microcarriers 2 and the restriction means 4 are preferably those described above. Consequently, the person skilled in the art will recognize that the steps (a) to (c) of the method for performing multiplexed assays disclosed herein as a second aspect of the invention actually form a multiplexed assay device of the first aspect of the invention. The descriptions of each of these two aspects of the invention can therefore be understood in the context of the other aspect.

For multiplexing purposes, the microchannel 1 is preferably loaded with different sets of microcarriers 2, each set having a different functionalization. All sets are present in the reaction chamber before the sample is flown and they undergo the assay simultaneously. As more than one set of functionalized microcarriers 2 are used and the microcarriers' position does not need to be not controlled, the various sets of microcarriers 2 need to be distinguishable from each other, i.e. there must be a way to determine the function of the microcarriers 2 when they are in the reaction chamber 1, independently of their position within the microchannel 1. This is done by using encoded microcarriers 2 wherein the code is indicative of the function. Examples of codes were outlined above. For multiplexing techniques, it is also desirable that the microcarriers can be distinguished and/or identified even in the absence of a signal produced by an analyte, i.e. independently of the performance of the assay (i.e. the technique must not rely on the presence of the analyte to reveal to which set a microcarrier belongs to) since there are embodiments where sets might not be revealed in case of absence of the corresponding target thus rendering quality control difficult and also significantly limiting the number of different sets that can be used (i.e. the level of multiplexing) because there is then a need to rely on methods where the reaction must be differentiable for each set (in case of fluorescent readouts, this is typically done by using different fluorophores but the level of multiplexing is then limited by their spectral characteristics and, in practice, this translates to a typical maximum of 5 or 6 different sets of microcarriers that can be used simultaneously). This can be achieved by using physical encoding techniques. For example the microcarriers can be individually encoded or otherwise produced with an attribute that is distinctive upon observation such as the code or attribute is indicative of the function.

In a preferred embodiment of the examples of codes outlined above in the description of the first aspect, the microcarriers 2 of the method have a disk-like shape and even more preferably, they have a code comprising traversing holes 21, preferably also including an orientation mark 20. Accordingly, the microchannel 1 has preferably a flat shape with a rectangular cross-section and the microcarriers 2 are arranged in a monolayer within the microchannel 1 (as in FIG. 6).

Step (b) can be achieved by flowing a fluid 9 comprising microcarriers 2 in suspension through an inlet 5 that connects to the entry 14 of the microfluidic channel 1, preferably through an enlarged section 6. As explained above, the practical implementation of this step is facilitated by the fact that the cross-section of the microchannel 1 is such that at least two microcarriers can stand side by side in the microfluidic channel 1 over its entire length. Step (b) can also be accompanied by a tapping of the assay device comprising the microchannel. This would facilitate the fact that microcarriers can pass each other, as allowed by the geometry of the setup, in the occurrence where a microcarrier would be blocked by an obstacle.

For step (b), it is preferable to allow more than strictly two microcarriers to be arranged side by side without touching the walls of the microchannel. Typically, allowing 3 (three) to 50 (fifty) microcarriers to side by side would facilitate the preparation of the setup as it allows reducing risks of clogging the entry of the microchannel and also cope with obstacle or debris that might be in the microchannel.

Step (c) is implemented by the use of a restriction means as outlined in the description of the restriction means above. The microcarriers 2 have their movement in the longitudinal direction restrained or are immobilized within the microchannel 1 while still letting the fluids flow through.

In Step (d), the sample possibly comprising the molecule(s) of interest is flown through the microchannel 1 and thus enters in close contact with the microcarriers 2. This may be done by using several techniques including pressure, electric potential (electro-osmotic flow), capillarity, gravity or centrifugal forces. In a preferred embodiment, the microchannel 1 is connected on one end to one or more inlets 5 (as explained above) and on the other end to one or more outlets, which allows the fluids to be moved by applying a differential of pressure between the one or more inlets and the one or more outlets, thus creating a pressure driven flow (PDF). Positive pressures and/or negative pressures (suction) can be applied to the one or more inlets and/or outlets by using pumping or pneumatic mechanisms. Thus, in one embodiment, the fluids 9 are moved by applying a positive pressure in an inlet connected to the microchannel and/or a negative pressure (suction) in an outlet connected to the microchannel. The fluids 9 can be flown in a continuous manner or in stop-flow manner (i.e. a sequence of moving fluids 9 and static fluids 9 in the microchannel).

The speed at which the sample 9 should flow, and thus the time that a molecule of interest passes in proximity to a microcarrier 2, can be optimized based on the diffusion speed of the target molecules 3 and the concentration of microcarriers 2 coated with receptors 10 for the target molecule 3.

Since the microcarriers 2 have their longitudinal movement restricted in the reaction chamber, it is easy to perform additional assay steps, if needed. This can simply be done by flowing various fluids 9 sequentially or simultaneously, for example to perform a washing or addition of new reagents, without requiring any particular manipulation of the microcarriers 2.

In one embodiment, the sample 9 is flown back and forth within the microchannel 1. Preferably, this movement is optimized to occur in a distance corresponding to the average distance between two microcarriers 2 having ligands 10 for the same target molecule 3. An embodiment wherein the sample 9 is moved back and forth can be achieved by using stopping means 4 based on forces acting on the microparticles 2 (such as magnetic forces) or by using an "activable" stopping means 4 near the entry 14 of the microchannel 1 (such as the compression of a part of the microchannel 1) to allow for the introduction of the microcarriers 2 before activating the stopping means 4.

In a further embodiment, the sample 9 is recirculated throughout the entire microchannel 1 by providing a fluidic connection from the outlet to the inlet and a means to actuate the fluids such as a peristaltic pump.

Recirculation or back and forth motion of the sample 9 is useful in situations where it is difficult to control the speed of the sample 9 and/or in case of very diluted samples 9.

The identification step (e) can be performed before, during or after the flowing of the sample (step d). It can also be performed simultaneously with or after the detection of the reaction (step f), in particular when the microcarriers 2 are identifiable independently from the performance of the assay, e.g. by combining the methods that are used for both aims, for example by using similar optical methods such as image capture and analysis for both identifying the sets and detecting the reactions. The identification is achieved by using encoded microcarriers 2 as already described above in several passages. Although their position in the microchannel 1 is not controlled, the different sets of microcarriers 2 of the invention can be identified and/or distinguished when they are in the microchannel 1 based on intrinsic characteristics that do not need to be revealed by the presence of target molecules, i.e. independently from the performance of the assay and independently on their position within the microchannel 1, for example by a code in the form of holes or by the shape of the microcarriers.

The detection step (f) can be performed during the flowing of the sample (step d) in order to get kinetic information on the progress of the reaction as the assay proceeds or after step (d) for end-point readout. It is also possible to perform the identification of the various sets before the flowing of the sample (step d). The detection step may e.g. involve the observation of the microcarriers (e.g. optical detection) or the sensing of the microcarriers (e.g. magnetic detection), either one by one or several simultaneously, for example by way of wide field observation techniques. The microcarriers 2 of the method disclosed herein are preferably the microcarriers 2 described above.

In addition to performing the assay, a biological readout is done to determine which microcarriers 2 have reacted and, optionally, to which degree (see step f). In a preferred embodiment, the microchannel 1 is designed to allow the observation of the microcarriers 2 directly inside the microchannel 1 by letting observable signals traverse at least one side on the portion containing the microcarriers 2. In a much preferred embodiment, the microchannel 1 is transparent on at least one side and on a portion to allow for optical observation. Alternatively or additionally, the microchannel 1 can also be permeable to magnetic fields or electromagnetic radiation and allow magnetic or electromagnetic sensing of the microcarriers to identify the various sets and/or perform biological readout (e.g. using magnetic labels).

In a preferred embodiment, the microcarriers 2 have a monolayer arrangement and the microchannel 1 is transparent in at least one side allowing for simple direct optical observation of all the microcarriers 1 individually. If the microcarriers are not in a monolayer arrangement, more complex confocal optical techniques can be used provided that the microcarriers are (semi)transparent.

Biological readout is typically performed by generating an observable signal, preferably an optically observable signal, when the binding occurs, for example, by a luminometric response or a magnetic response or other type of electromagnetic emission, typically using a complementary labelled molecule. The reaction may be indicated by a colorimetric, chemiluminometric, quantum dots emission and/or fluorometric response. The biological readout may also give quantitative information (i.e. information on the quantity of analyte present in the sample) by measuring the intensity of the signal that is generated by the reaction. As several sets of microcarriers are used in a reaction chamber, it is necessary that the signal generation mechanism is co-localized in the microcarrier and not released in the bulk of the solution. Typically, the reaction is revealed by using a complementary molecule that attaches to the complex formed by the ligand and the target molecule (if the latter is present in the sample). Alternatively, we can have a complex comprising a fluorophore and a quencher attached to the surface of the microcarrier and a reaction that is designed to cleave the quencher while leaving the fluorophore tethered to the surface, therefore generating a signal on the surface of the microcarrier. The biological readout may also involve label-free detection techniques known in the art, i.e. for example Surface Plasmon Resonance (SPR) or electrical methods (e.g. change in conductivity).

As illustrated in FIG. 5, a preferred method consists in preparing a setup where the microcarriers 2 are in a monolayer arrangement and in positioning a sensor, preferably an optical sensor, to observe the microcarriers 2 directly in the area where the reaction occurs, i.e. within the reaction chamber 1, preferably without moving the microcarriers 2. The sensor could be a wide field sensor that observes/senses multiple microcarriers 2 at a time (e.g. a CCD or a CMOS photosensor array coupled with the necessary optic means such as lenses and objectives to form a setup akin to a microscope) or a narrow field sensor (e.g. a photodiode, a photomultiplier, or a confocal scanner, or a magnetic sensor) that observes/senses one microcarrier at a time. For optical sensors, the microchannel 1 needs to be transparent on at least the side from which the microcarriers are observed. Preferably, a wide field sensor is used to "capture" an image or a series of images of the microcarriers 2 within the reaction chamber 1 and reveal reactions through image processing. This technique may be combined with the detection of the codes to identify the sets of microcarriers provided that the encoding mechanism is based on optical contrast that can be detected with similar optics (for example by using an encoding mechanism based on traversing holes). A narrow field sensor can also be used but needs to be moved in order to pass by all the microcarriers 2 and generate a signal that can be analyzed to reveal the reactions. As the position of the microcarriers 2 is relatively free within the microchannel 1, the narrow field sensor can be used in a manner where it constructs an image by scanning the reaction chamber 1. Alternatively, several narrow field sensors can be used to observe several zones of the microchannel 1 simultaneously. It is also possible to combine the use of a wide field sensor for the identification of the microcarriers 2 together with a narrow field sensor for the detection of the reaction.

Figure 9:
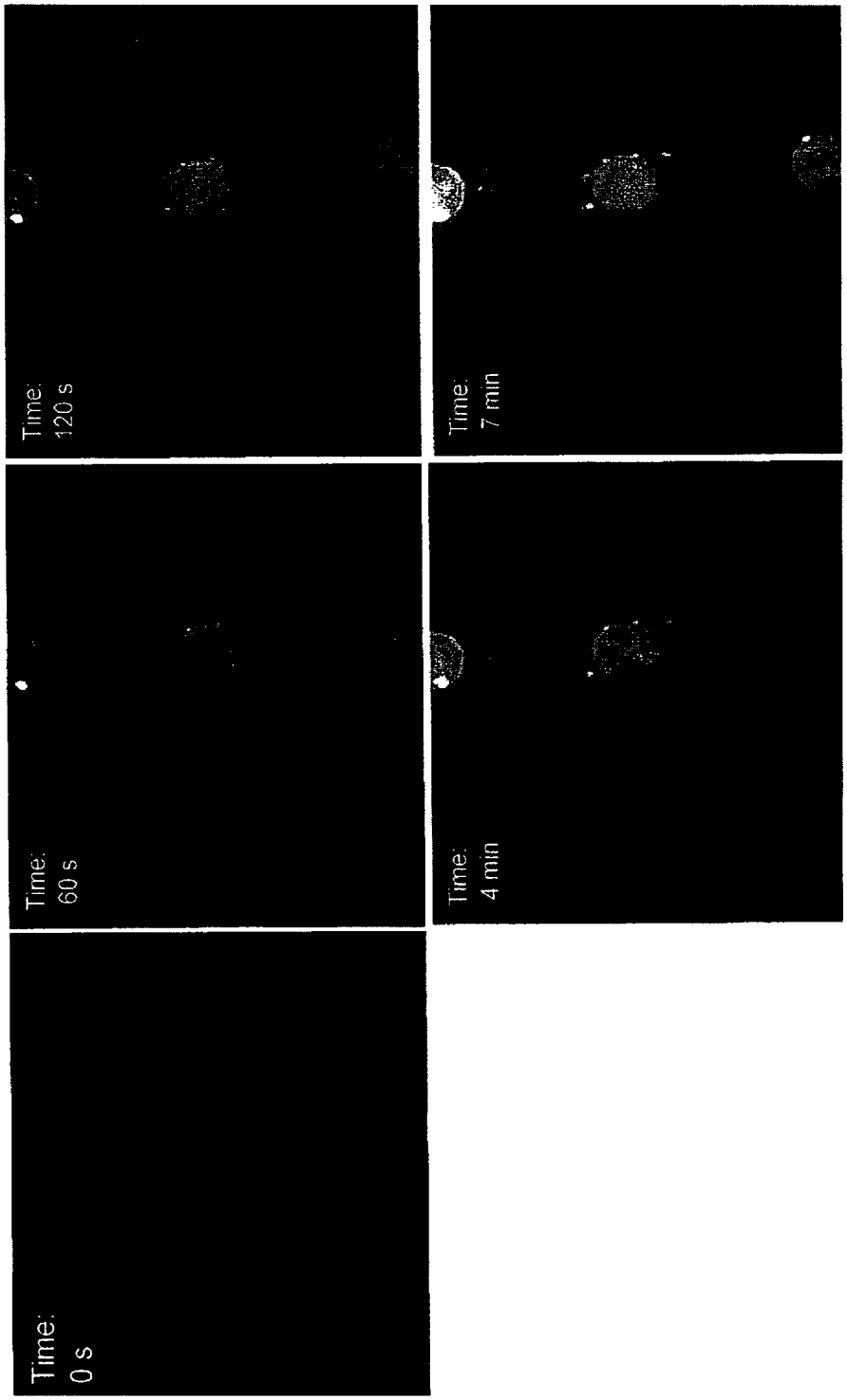
FIG. 9 illustrates how the biological readout can be performed over time while the assay occurs to provide, information on the kinetics of the reaction. The device is very efficient in terms of mass transfer as it is able to detect hybridization reactions in a few seconds (performed at target concentration of 200 nM). The picture was taken by a CCD camera under fluorescent light.

In the embodiments where the microcarriers 2 are observed directly in the reaction chamber 1, the stopping means 4 does not need to be removed and the microcarriers 2 do not need to be released for detection purposes; however, the microchannel 1 is preferably transparent at least on one side and/or at least on one portion allowing the optical observation of the microcarriers 2. This embodiment also allows for kinetic reading of the reaction. Indeed it is possible to observe the biological indications as the assay progresses and therefore get timely information on the reaction kinetics (see FIG. 9). Alternatively to optical sensors, other types of sensors, such as magnetic sensors or spectrometric sensors, could also be used if the assay is designed to change the magnetic signature or the emission spectrum of the microcarriers 2 when a reaction occurs. This can be achieved, for example, by using "magnetic labels" attached to complementary antibodies in the same fashion as fluorescent labels are used.

Another alternative consists in releasing or moving, at the end of the assay, the microcarriers 2 through another portion of the microchannel 1 (an observation portion or window) and read the biological signals as they pass, similar to what is done in Fluorescent-Activating Cells Sorting [FACS] or, alternatively, to retrieve the microcarriers 2 through an outlet well and place them in another device for observation, for example in a microscope slide positioned in a fluorescent microscope. This method allows only for end-point biological readout but does not allow for kinetic readout. Here again, a wide field sensor (such as a CCD or C-MOS photo-sensor array) or a narrow field sensor (such as a photodiode) may be used. This can also be combined with the detection of the code to identify the sets of microcarriers 2. For said purpose, the restriction of the longitudinal movement must be removed as explained above, e.g. by removing the stopping means 4 or by remove the magnetic field.

In step (f), the observation of the biological readout is correlated with the identity of a microcarrier 2 as observed in step (e). This correlation of two observations (i.e. the observation of the identity and the observation of the biological signal) may e.g. done either by combining the two observations in one (i.e. using a same signal or a same optical image) or by using the position of the microcarriers to correlate the two observations (i.e. by using two signals or optical images that correspond to the same spatial position where the microcarrier 2 is present). The static arrangement of the microcarriers 2 facilitates this correlation as the two observations can be separated in time, e.g. when the identification step (e) is performed before flowing the sample (step d). In a preferred embodiment, the identification step (e) is performed essentially simultaneously with the biological readout step (f) in order to ensure that any inadvertent motion of the microcarriers 2 does not prevent correlating the identity of the microcarriers 2 with their biological signal. This can be achieved, for example, by taking two images with a CCD or a C-MOS camera simultaneously or in a very short period of time after or during the flowing of the sample (step d). The first image, typically a bright field image, is used for identifying the microcarriers 2 whereas the second image, typically a fluorescent image, is used to perform the biological readout. Alternatively, the identification and the biological readout can be based on a unique observation (for example a same image). The latter is applicable to embodiments where the microcarriers 2 are released in an observation area and observed as they pass.

Chip

Figure 10:
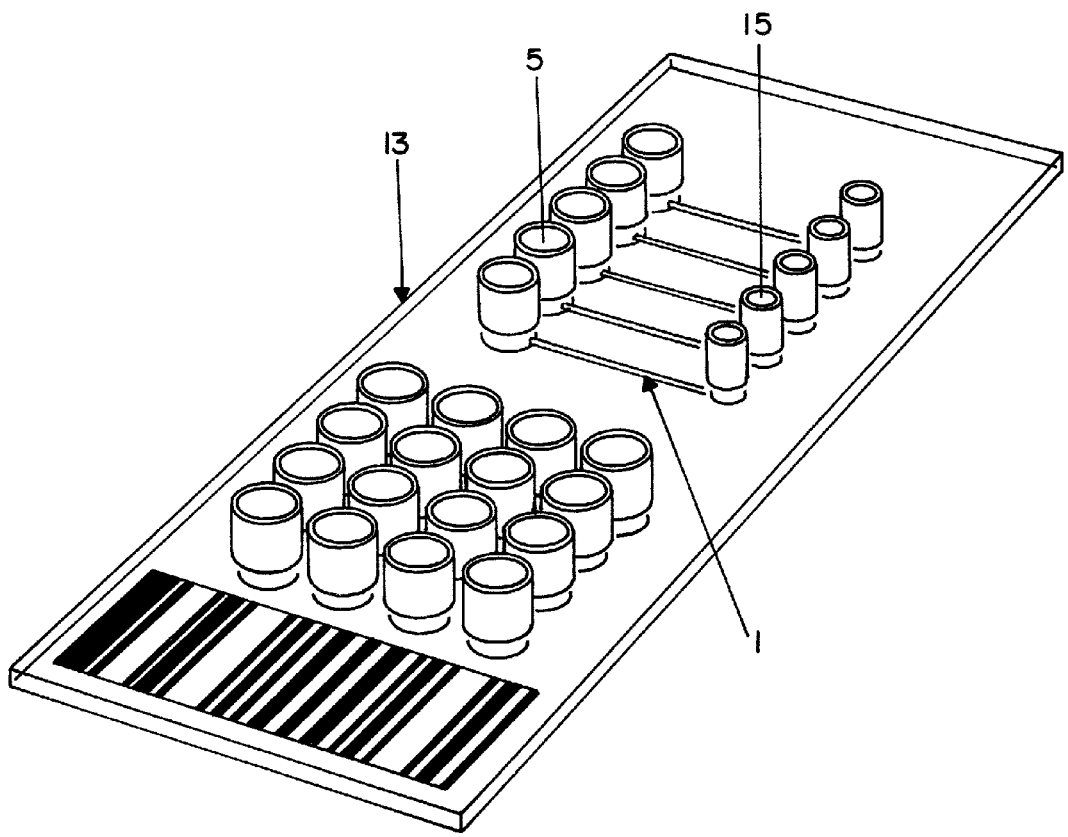
FIG. 10 illustrates a chip 13 for multiplexing. Said chip comprises several microchannels 1 containing several sets of functionalized microcarriers. The microchannels 1 connect to an inlet 5 and to an outlet 15. The microcarriers are disk-shaped and encoded (such as described above for FIG. 7).

In another aspect, the invention provides a chip 13 for multiplexing. Said chip 13 comprises the assay device described in the first aspect of the invention. An exemplary chip 13 is shown in FIG. 10. Said chip 13 may for example be used for diagnostic purposes. In a much preferred embodiment, the microcarriers 2 can be observed without the need to release the microcarriers 2 from the microchannel 1.

Example 1

Figure 16:
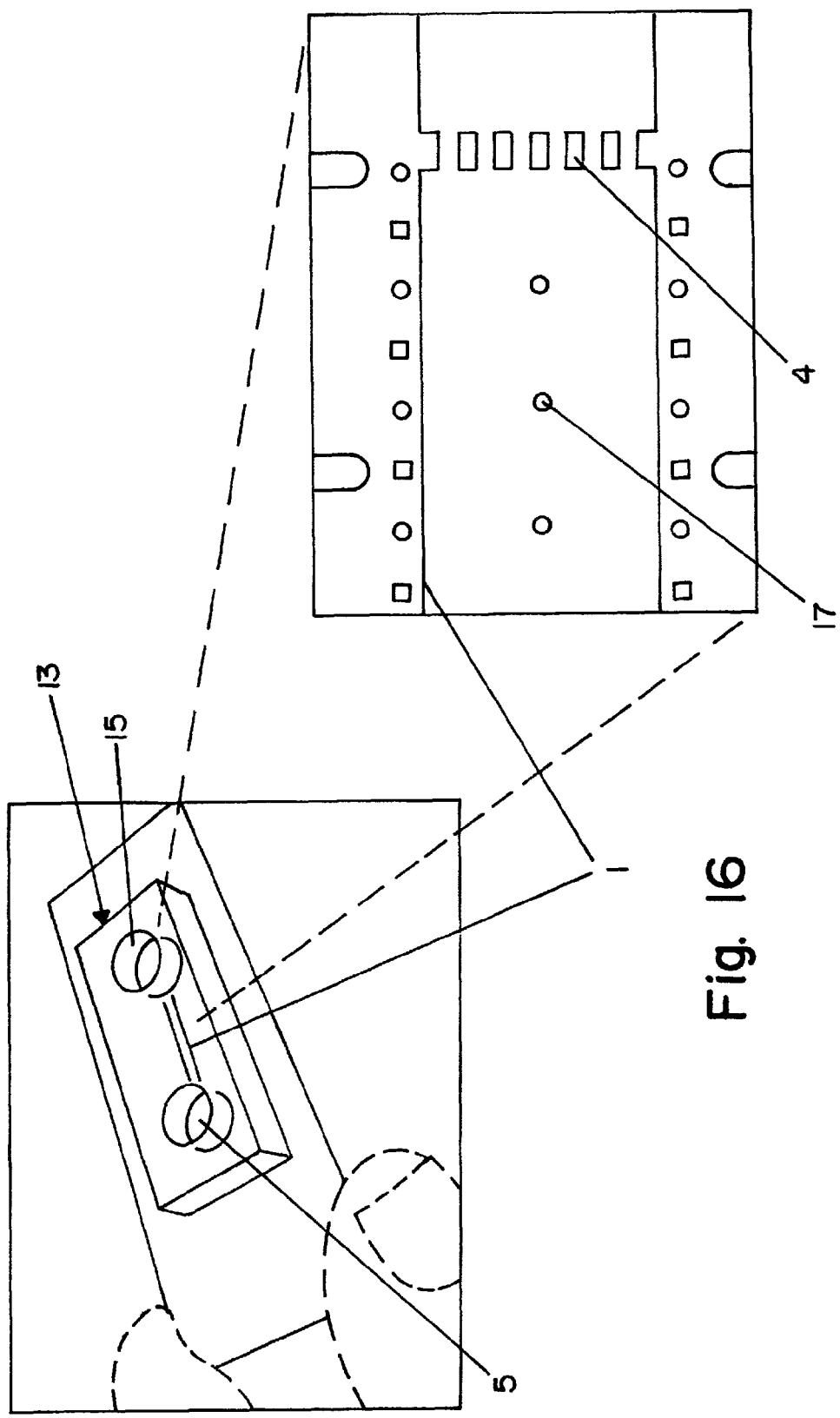
FIG. 16 shows line drawings of two pictures of an exemplary embodiment. A chip 13 made using PDMS molding techniques and bonded to a glass microscope slide (as described in Fundamentals and Applications of Microfluidics by Nam-Trung Nguyen and Steve Wereley, ISBN: 9781580533430, chapter 3) comprises a microchannel 1 that connects, at one end, to an inlet 5 and, at the other end, to an outlet 15. A stopping means 4 consisting of a filter structure made of rectangular pillars is build at the exit of the microchannel 1. In addition, cylindrical pillars 17 are built in the microchannel 1 to help stabilizing the height of the microchannel (i.e. avoiding that it compresses) when applying negative pressures.

A setup containing a microchannel connected to an inlet well and to an outlet well and comprising a filter structure as well as stabilizing central pillars (see FIG. 16) was fabricated using PDMS molding techniques and bonded to a glass microscope slide (as described in Fundamentals and Applications of Microfluidics by Nam-Trung Nguyen and Steve Wereley, ISBN: 9781580533430, chapter 3).

Figure 17:
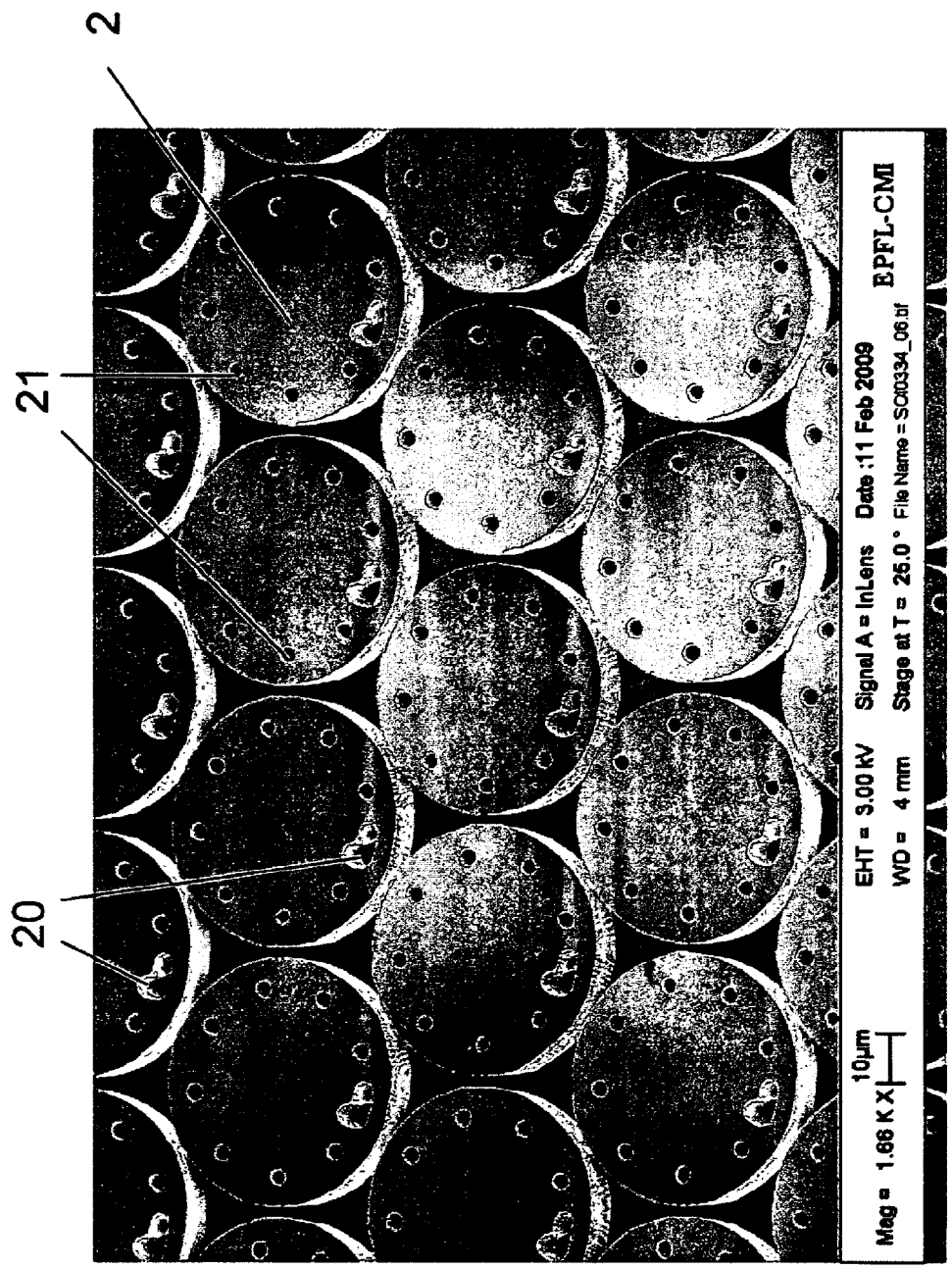
FIG. 17 shows a picture of a wafer comprising silicon microparticles that are not yet released. The microparticles have a disk-like shape and are encoded by a pattern of traversing holes 21. The microcarriers have a diameter of 50 microns and include an L-shaped orientation mark 20.

Disc shaped silicon microcarriers with a pattern of traversing holes on the periphery (to serve as the code) were produced. This was done in a clean room environment using wafer-based microfabrication techniques that allows producing several million microcarriers with a diameter of 50 micrometers and a thickness of 10 micrometers. The process flow that was composed of the following steps:

1) Providing an SOI (silicon-on-insulate) wafer (4 inch in diameter, 380 µm thick substrate wafer, 1 µm thick of BOX, 10 µm of device layer);

2) Delineating the shape of the microcarriers and their code (see FIG. 17) by using traditional photolithography techniques (spin-coating of a photosensitive protective resist, UV illumination through a mask, development, etching of the silicon of the device layer all through, and finally strip of the resist);

3) Preparing the lift-off of the microcarriers by etching away the BOX layer of the wafer;

4) Depositing an oxide layer of a thickness of approx. 110 nm by PECVD (Plasma-enhanced chemical vapor deposition) on top of the microcarriers. This layer is necessary to ensure an appropriate fluorescent signal on silicon particles (Bras, M., et al., Optimisation of a silicon/silicon dioxide substrate for a fluorescence DNA microarray. Biosensors & bioelectronics, 2004. 20(4): p. 797-806; Voile, J. N., et al., Enhanced sensitivity detection of protein immobilization by fluorescent interference on oxidized silicon. Biosensors and Bioelectronics, 2003. 19(5): p. 457-464);

5) Releasing the microcarriers from the substrate by dipping the wafer into a liquid solution such as acetone under sonication.

This procedure was repeated to produce two sets of microcarriers with several different codes.

Approximately 300,000 microcarriers of each code were then functionalized with primary amines on the surface by reaction with 10% v/v (3-aminopropyl)triethoxysilane in 1 mL of acetone at room temperature for 1 h with agitation. The microcarriers were pelleted and resuspended in 1 mL of 10 mM borate buffer, 150 mM NaCl pH 8.2 containing 0.1% Tween-20 (BBST). The amino groups on the surface of the microcarriers were activated by adding 800 µL of 10% v/v glutaraldehyde in BBST. The microcarriers were agitated in this solution at room temperature for 1 h. Following the activation step, the microcarriers were washed in 1 mL of BBST 3 times.

After that, two sets of microcarriers were coated with biological probes P1 (5'-CAA CCC CAG CTA ATA TTA TT-3') (SEQ ID NO: 1) and P2 (5'-TGG GTA AGT TAG GGC GAT GG-3') (SEQ ID NO: 2), respectively, by adding a solution of 500 nM amino-modified (5'- or 3'-) oligonucleotide (P1 or P2) in BBST. The microcarriers were then agitated in this solution at room temperature for 1 h. After the washing steps as described above with BBST, the unreacted functional groups were blocked by reaction with 35 mM glycine in BBST at room temperature for 15 min. The microcarriers were washed with BBST twice and then stored in the same buffer.

A master mix suspension of the two sets of microcarriers was prepared by mixing thoroughly 10 µL of the microcarrier suspension from each set as prepared above. The mix of the two sets of functionalized microcarriers was then loaded in the microchannel by pipetting the master mix suspension in the inlet and applying negative pressure in the outlet to suck the master mix suspension of microcarriers into the microchannel. The PDMS microchannel was previously primed with ethanol to improve hydrophilic behavior.

A sample solution of targets T1 (5' Cy 5-AAT AAT ATT AGC TGG GGT TG 3') (SEQ ID NO: 3) complementary with P1 was prepared by providing a solution of 200 nM oligonucleotide T1 labeled with Cy5 fluorophore at the 5' end in 5×SSPE (containing 125 mM phosphate buffer, 745 mM NaCl, 5 mM EDTA pH 7.4).

After removing any excess solution from the inlet well, this sample solution was added to the inlet well and flushed through the channel at room temperature for 5 min. After flushing the target sequence T1, the excess solution was removed from the inlet well and the microcarriers were washed by flushing 2×SSC (15 mM sodium citrate, 150 mM NaCl, pH 7) at room temperature for 1 min. The fluorescence signal on the two set of microcarriers was observed, through the glass layer, on a fluorescence microscope (Zeiss Axiovert 135) with Cy5 filter set. The results of the experiment may be captured by a cooled CCD camera (Hamamatsu ORCA C4742-80-12AG camera).

While there are shown and described presently preferred embodiments and examples of the invention, it is to be distinctly understood that the invention is not limited thereto but may be otherwise variously embodied and practiced within the scope of the following claims.

The invention claimed is:

1. An assay device comprising:
    a reaction chamber located in a microchannel;
    at least two sets of individually encoded functionalized microcarriers;
    at least one side of the microchannel being configured to allow for optical observation or identification of said microcarriers in the microchannel;
    each said microcarrier of one of the at least two sets having identical functionalization;
    a cross-section of the reaction chamber having a height and a width that is greater than the height;
    a cross-sectional width of each said microcarrier being less than half of the width of the cross-section of the reaction chamber such that at least two microcarriers arranged side by side without touching each other can pass each other in a longitudinal direction when they move at different speeds within the microchannel; and
    a movement restricting device structured and arranged to limit movement of the microcarriers.

2. The assay device of claim 1, wherein the microcarriers are wafer-shaped and the cross-section of the reaction chamber inside the microchannel is rectangular.

3. The assay device of claim 1, wherein the microcarriers comprises one of:
    openings; and
    a pattern of traversing holes.

4. The assay device of claim 1, wherein the microchannel comprises an enlarged cross-section inlet structured and arranged to allow the microcarriers to be introduced in a random sequence.

5. A method for performing a multiplexed assay based on microcarriers comprising the steps of
    providing an assay device according to claim 1;
    at least partially filling a microchannel with at least two sets of encoded microcarriers;
    restricting the movement of said microcarriers in a longitudinal direction while still letting fluid flow through;
    identifying said microcarriers; and
    performing a biological read-out in correlation with the identifying.

6. The method according to claim 5, wherein the identifying comprises observing each microcarrier directly in a reaction chamber of the microchannel.

7. The method according to claim 5, wherein one of:
    the performing occurs at a same time as a sample containing said microcarriers moves through the microchannel;
    the performing occurs at a same time as said identifying; and
    the identifying occurs before a sample containing said microcarriers moves through the microchannel.

8. The method according to claim 5, wherein the identifying occurs via at least one of:
    a transparent side of the microchannel;
    an array of optical sensors coupled with a optic device;
    a CCD; or
    a C-MOS photo-sensor.

9. The assay device of claim 1, wherein a code of each said microcarrier is indicative of its functionalization.

10. The assay device of claim 1, wherein the movement restricting device is arranged downstream of an inlet of the reaction chamber.

11. The assay device of claim 2, wherein a shape of the cross-section of the reaction chamber and a shape of the microcarriers restrict movement of the microcarriers inside the microchannel along one direction other than the longitudinal direction, while the microcarriers move along the longitudinal direction.

12. The assay device of claim 11, wherein the shape of the microcarriers and the shape of the cross-section of the reaction chamber constrain the microcarriers to a monolayer configuration inside the microchannel.

13. The assay device of claim 1, wherein each microcarrier has a width and a width of the cross-section is larger than a sum of the widths of two microcarriers arranged side by side.

* * * * *